US010307051B2

(12) United States Patent
Ootsuki

(10) Patent No.: US 10,307,051 B2
(45) Date of Patent: Jun. 4, 2019

(54) IMAGE PROCESSING DEVICE, METHOD OF IMAGE PROCESSING, AND SURGICAL MICROSCOPE

(71) Applicant: SONY CORPORATION, Tokyo (JP)

(72) Inventor: Tomoyuki Ootsuki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/522,106

(22) PCT Filed: Sep. 30, 2016

(86) PCT No.: PCT/JP2016/078981
§ 371 (c)(1),
(2) Date: Apr. 26, 2017

(87) PCT Pub. No.: WO2017/065018
PCT Pub. Date: Apr. 20, 2017

(65) Prior Publication Data
US 2018/0008139 A1 Jan. 11, 2018

(30) Foreign Application Priority Data

Oct. 15, 2015 (JP) .................................. 2015-203409

(51) Int. Cl.
A61B 3/00 (2006.01)
A61B 3/10 (2006.01)
(Continued)

(52) U.S. Cl.
CPC .............. A61B 3/0025 (2013.01); A61B 3/10 (2013.01); A61B 3/102 (2013.01); A61B 3/107 (2013.01);
(Continued)

(58) Field of Classification Search
CPC combination set(s) only.
See application file for complete search history.

(56) References Cited

U.S. PATENT DOCUMENTS

2011/0230751 A1 9/2011 Kersting
2012/0188357 A1 7/2012 Hiramatsu et al.
(Continued)

FOREIGN PATENT DOCUMENTS

JP 2012-506272 A 3/2012
JP 2012/506272 A 3/2012
(Continued)

OTHER PUBLICATIONS

International Search Report dated Nov. 1, 2016 in PCT/JP2016/078981 filed Sep. 30, 2016.

Primary Examiner — Brenda C Bernardi
(74) Attorney, Agent, or Firm — Oblon, McClelland, Maier & Neustadt, L.L.P.

(57) ABSTRACT

The present technology relates to an image processing device, a method of image processing, and a surgical microscope that can detect and report a dangerous condition on the basis of a tomographic image during eye surgery.
An image processing device includes: a dangerous condition detection unit configured to detect a dangerous condition on the basis of a tomographic image of an eye acquired during surgery of the eye; and a control information generation unit configured to generate and output control information used to manage the detected dangerous condition. The present technology is applicable to, for example, a surgical system used for eye surgery or other surgical procedures.

23 Claims, 34 Drawing Sheets

(51) Int. Cl.
*A61B 3/13* (2006.01)
*G06T 7/00* (2017.01)
*G06T 7/60* (2017.01)
*A61B 17/00* (2006.01)
*A61B 3/107* (2006.01)
*A61F 9/007* (2006.01)
*A61F 9/008* (2006.01)

(52) U.S. Cl.
CPC ............... *A61B 3/13* (2013.01); *A61F 9/007* (2013.01); *A61F 9/00736* (2013.01); *G06T 7/0016* (2013.01); *G06T 7/60* (2013.01); *A61B 2017/00119* (2013.01); *A61B 2017/00199* (2013.01); *A61F 2009/00851* (2013.01); *G06T 2207/10101* (2013.01); *G06T 2207/30041* (2013.01)

(56) References Cited

U.S. PATENT DOCUMENTS

| | | | |
|---|---|---|---|
| 2014/0205169 A1* | 7/2014 | Yamakawa | G06T 7/0012 382/131 |
| 2014/0221822 A1 | 8/2014 | Ehlers et al. | |
| 2016/0338589 A1* | 11/2016 | Carrasco-Zevallos | A61B 3/102 |
| 2018/0049635 A1* | 2/2018 | Uji | A61B 3/0033 |

FOREIGN PATENT DOCUMENTS

| | | |
|---|---|---|
| JP | 2014-140490 A | 8/2014 |
| WO | 2011/059018 A1 | 5/2011 |

\* cited by examiner

IMAGE PROCESSING DEVICE, METHOD OF IMAGE PROCESSING, AND SURGICAL MICROSCOPE

TECHNICAL FIELD

The present technology relates to image processing devices, methods of image processing, and surgical microscopes. More particularly, the present technology relates to an image processing device, method of image processing, and surgical microscope, capable of detecting and reporting a dangerous condition on the basis of a tomographic image during eye surgery.

BACKGROUND ART

In eye surgery, a front image obtained by capturing the eye from the front and a tomographic image that is a cross-sectional image in the depth direction of the eye are used as an image for diagnosis and analysis. In one example, Patent Literature 1 discloses an ophthalmic analysis apparatus that outputs a result obtained by analyzing a tomographic image of the eye, which is acquired by optical coherence tomography (OCT). The OCT is a technique of generating an image by irradiating an eye subject to surgical procedures with near infrared light and by reconstructing waves reflected by each tissue of the eye.

CITATION LIST

Patent Literature

Patent Literature 1: JP 2014-140490A

DISCLOSURE OF INVENTION

Technical Problem

However, there has been no detection or report of a dangerous condition such as development of complications based on a tomographic image during eye surgery in the related art.

The present technology is made in view of such a situation, and it is intended to detect and report a dangerous condition on the basis of a tomographic image during eye surgery.

Solution to Problem

An image processing device according to a first aspect of the present technology includes: a dangerous condition detection unit configured to detect a dangerous condition on the basis of a tomographic image of an eye acquired during surgery of the eye; and a control information generation unit configured to generate and output control information used to manage the detected dangerous condition.

A method of image processing according to a second aspect of the present technology includes the steps of: detecting, by an image processing device, a dangerous condition on the basis of a tomographic image of an eye acquired during surgery of the eye; and generating and outputting, by the image processing device, control information used to manage the detected dangerous condition.

A surgical microscope according to a third aspect of the present technology includes: a tomographic image capturing unit configured to capture a tomographic image of an eye as a target of surgery; a dangerous condition detection unit configured to detect a dangerous condition on the basis of the tomographic image of the eye acquired during surgery; and a control information generation unit configured to generate and output control information used to manage the detected dangerous condition.

According to the first to third embodiments of the present technology, the dangerous condition is detected on the basis of the tomographic image of the eye acquired during the eye surgery, and control information used to manage the detected dangerous condition is generated and is output.

The image processing device may be an independent device, or may be an internal block that constitutes a single device.

Advantageous Effects of Invention

According to the first to third embodiments of the present technology, it is possible to detect and report the dangerous condition on the basis of the tomographic image during the eye surgery.

Note that the effects described herein are not necessarily limited, and may be any of the effects described in the present disclosure.

MODE(S) FOR CARRYING OUT THE INVENTION

Figure 1:
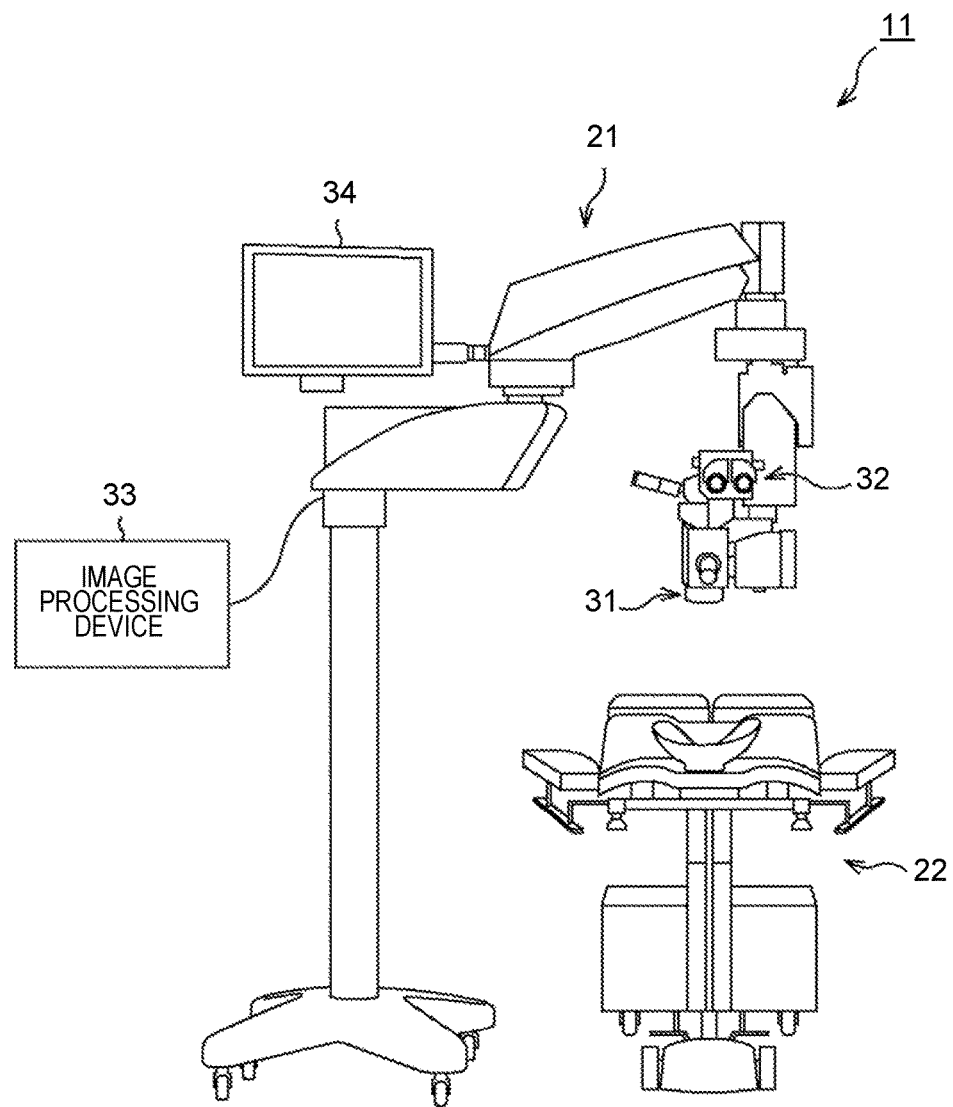
FIG. 1 is a diagram illustrating a configuration example of an embodiment of a surgical system to which the present technology is applied.

The best modes for carrying out the present technology (hereinafter referred to as an embodiment) are described below. The description is given in the following order.
1. Configuration example of surgical system
2. Block diagram related to detection and reporting of dangerous condition
3. Processing procedure of dangerous condition detection and reporting processing
4. Detection example of shallow anterior chamber
5. Detection example of IMS risk
6. Detection example of posterior capsule rupture
7. Detection example of nucleus drop
8. Detection example of implant misplacement
9. Detection example of iris prolapse risk
10. Configuration example of computer <1. Configuration Example of Surgical System>

FIG. 1 is a diagram illustrating a configuration example of an embodiment of a surgical system to which the present technology is applied.

The surgical system 11 illustrated in FIG. 1 is a system used for eye surgery, and has a surgical microscope 21 and a patient bed 22. The patient undergoes eye surgery while lying on the patient bed 22. In addition, an eye doctor who is a surgeon performs surgery while observing the eye of the patient using the surgical microscope 21.

The surgical microscope 21 has an objective lens 31, an eyepiece 32, an image processing device 33, a monitor 34, and the like, which are used to magnify and observe the patient's eye as a surgery target.

The image processing device 33 performs predetermined image processing on an image captured through the objective lens 31 to detect and output a dangerous condition during surgery.

The monitor 34 displays an image captured through the objective lens 31, or displays predetermined information generated by the image processing device 33, for example, reporting information that is used to report a dangerous condition during surgery (hereinafter also referred to as a dangerous condition) to the surgeon.

In the surgical system 11, in one example, the eye doctor looks through the eyepiece 32 and performs surgery while observing the patient's eye through the objective lens 31. In addition, the eye doctor perform surgery while checking an image displayed on the monitor 34 and predetermined information displayed on the monitor 34 by the image processing device 33.

Figure 2:
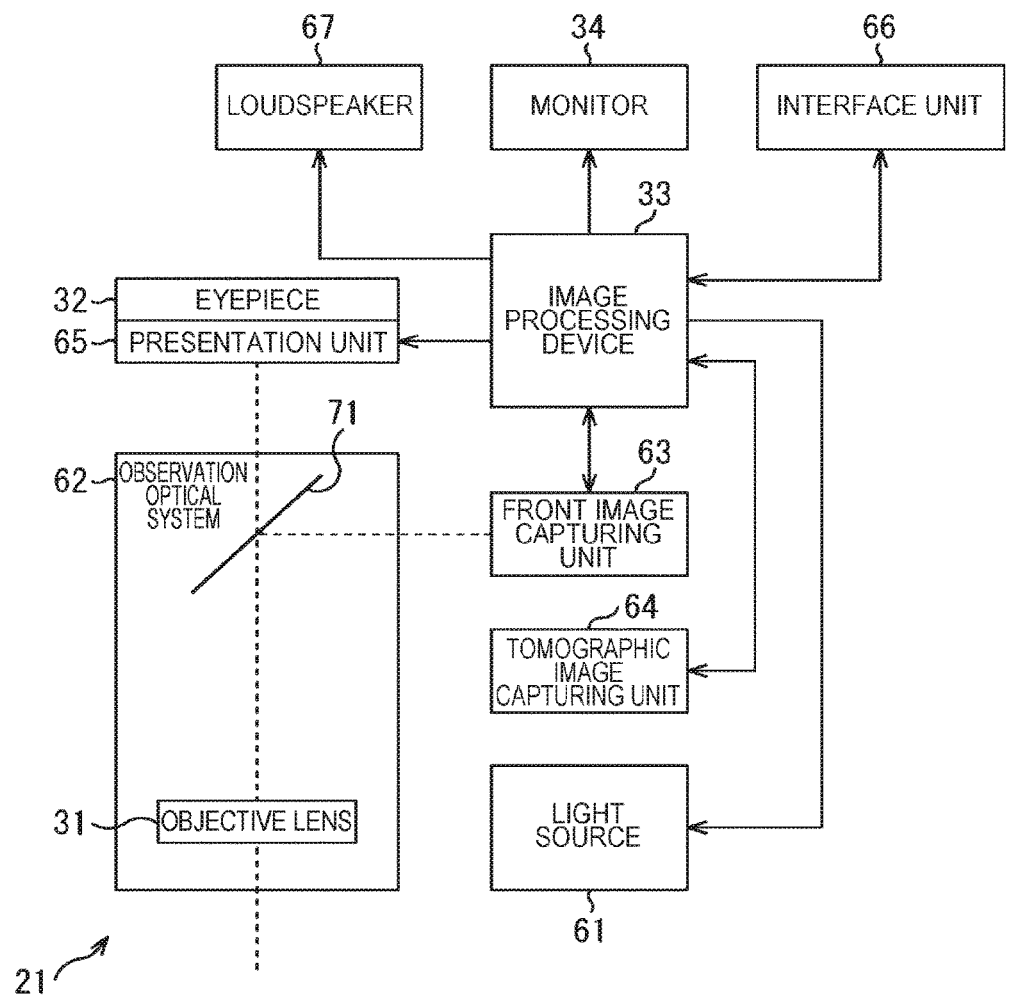
FIG. 2 is a block diagram illustrating a detailed configuration of a surgical microscope.

FIG. 2 is a block diagram illustrating the detailed configuration of the surgical microscope 21. Moreover, in FIG. 2, components corresponding to those in FIG. 1 are denoted with the same reference signs, and so the description thereof is omitted as appropriate.

The surgical microscope 21 is configured to include a light source 61, an observation optical system 62, a front image capturing unit 63, a tomographic image capturing unit 64, a presentation unit 65, an interface unit 66, and a loudspeaker 67.

The light source 61 emits illumination light under the control of the image processing device 33 and illuminates the patent's eye. In addition, the observation optical system 62 is composed of, for example, optical devices such as the objective lens 31, a half mirror 71, and other lenses (not shown), and guides light reflected from the patient's eye (observation light) to the eyepiece 32 and the front image capturing unit 63.

In other words, the light reflected from the patient's eye is used as the observation light and is incident on the half mirror 71 through the objective lens 31 or other lens (not shown). The approximately one half of the observation light incident on the half mirror 71 passes through the half mirror 71 without any change and is incident on the eyepiece 32 through the transmission presentation unit 65. On the other hand, the other half of the observation light incident on the half mirror 71 is reflected by the half mirror 71 and is incident on the front image capturing unit 63.

The front image capturing unit 63 is composed of, for example, a video camera or the like. The front image capturing unit 63 receives the observation light incident from the observation optical system 62 and converts the light into electric charges. Thus, the front image capturing unit 63 captures an image obtained by observing the patient's eye from the front, that is, captures a front image that is an image obtained by capturing the patient's eye from the substantially axial direction of the eye. The front image capturing unit 63 captures the front image under the control of the image processing device 33 and supplies the obtained front image to the image processing device 33.

The tomographic image capturing unit 64 is composed of, for example, an optical coherence tomography (OCT) meter, a Scheimpflug camera, or the like. The tomographic image capturing unit 64 captures a tomographic image that is an image of a cross section of the patient's eye under the control of the image processing device 33, and supplies the obtained tomographic image to the image processing device 33. Here, the tomographic image is an image of a cross section in a direction substantially parallel to the ocular axial direction of the patient's eye.

Moreover, the tomographic image capturing unit 64 acquires a tomographic image using, for example, infrared light on the basis of the interference principle, but the optical path of the infrared light at that time and a portion of the optical path of the observation light in the observation optical system 62 may be a common optical path.

The eyepiece 32 forms an optical image of the patient's eye by concentrating the observation light incident from the observation optical system 62 through the presentation unit 65. This allows the surgeon who looks through the eyepiece 32 to observe the optical image of the patient's eye.

The presentation unit 65 is composed of a transmission display device and is disposed between the eyepiece 32 and the observation optical system 62. The observation light incident from the observation optical system 62 passes through the presentation unit 65 and is incident on the eyepiece 32. The presentation unit 65 also presents (displays) the front image, the tomographic image, the reporting information, and the like, as necessary, which are supplied from the image processing device 33. In one example, the front image, the tomographic image, the reporting information, or the like may be presented in superposition with the optical image of the patient's eye, or may be presented near the optical image without interfering with the optical image.

The image processing device 33 controls the overall operation of the surgical microscope 21. In one example, the image processing device 33 changes the illumination condition of the light source 61 or the zoom magnification of the observation optical system 62. In addition, the image processing device 33 also controls the front image capturing unit 63 and the tomographic image capturing unit 64 so that they may acquire an image on the basis of information on an operation by a surgeon or other specialists, which is supplied from the interface unit 66.

The interface unit 66 is composed of, for example, a touch panel provided to be superimposed on the monitor, a controller, or a communication unit, and supplies information or the like depending on the operation by a surgeon or other specialists to the image processing device 33. The communication unit of the interface unit 66 receives an instruction from a remote controller (not shown), and communicates with an external device. In addition, the interface unit 66 outputs device control information or the like to the external device. The device control information or the like is used to control the external device and is supplied from the image processing device 33 when a dangerous condition is detected.

The monitor 34 displays the front image, the tomographic image, the reporting information, or the like depending on the control of the image processing device 33. In the case where a dangerous condition is detected during surgery, the loudspeaker 67 outputs sound such as buzzer sound and melody sound, a message (voice) such as "Detected", or the like to report the dangerous condition to the surgeon or other specialists. In addition, the surgical microscope 21 may be provided with a rotary lamp or indicator light (lamp) for reporting the dangerous condition to a surgeon or other specialists.

In the surgical system 11 having the configuration as described above, the image processing device 33 can detect a dangerous condition occurring during eye surgery and can report the dangerous condition to the surgeon using the monitor 34, the speaker 67, or the like. Such detection and reporting is based on the front image and the tomographic image acquired by the front image capturing unit 63 and the tomographic image capturing unit 64, respectively.

In the following, the description is given on the detection of the dangerous condition by the image processing device 33 and the reporting of the dangerous condition in a case where cataract surgery is performed even during the eye surgery as an example.

Figure 3:
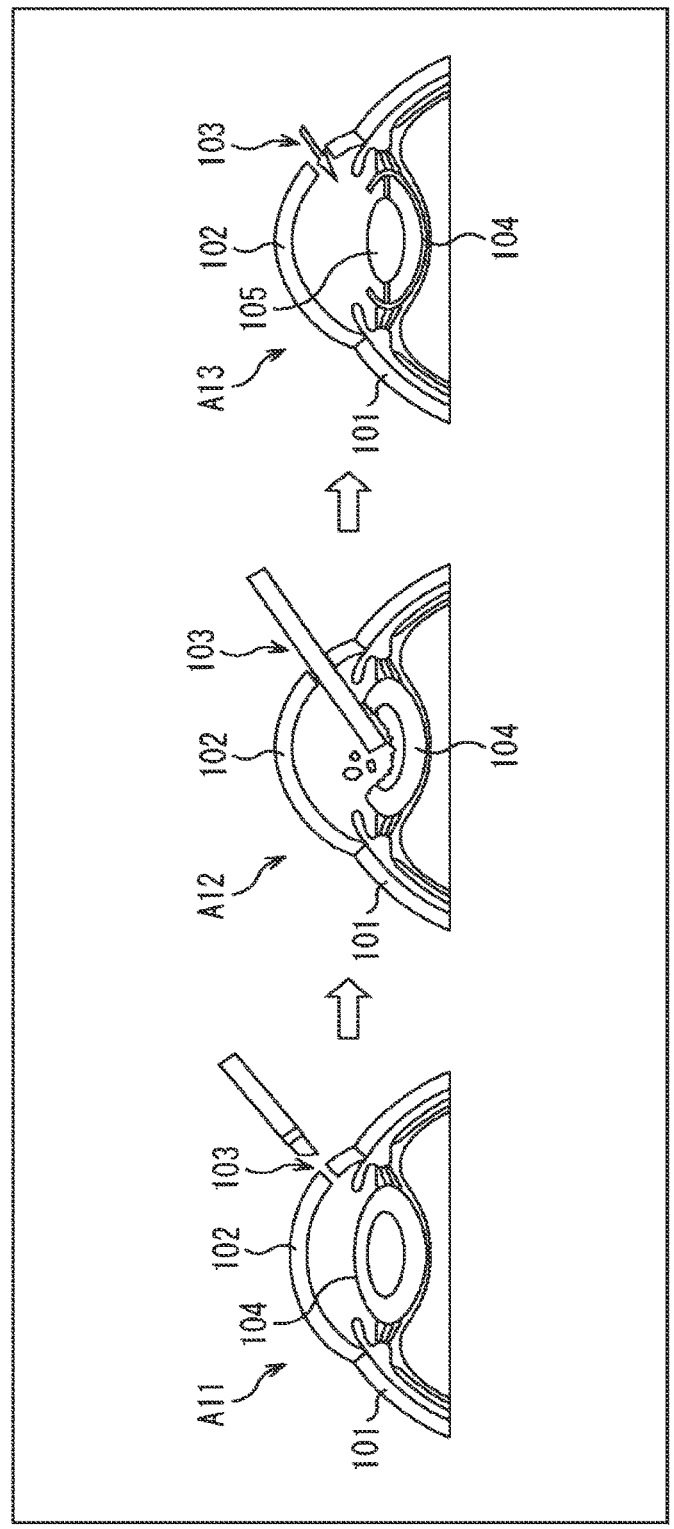
FIG. 3 is a diagram illustrated to describe briefly the cataract surgery.

Thus, a brief description on the cataract surgery is given with reference to FIG. 3.

In the cataract surgery, as shown by an arrow A11 in FIG. 3, a cornea 102 of an eyeball 101 of the patient is incised with a knife to define an incision 103. Then, a surgical instrument is inserted through the incision 103, and the anterior portion of the eye lens 104 inside the eyeball 101, that is, the anterior capsule portion is incised in a circular shape.

Then, as shown by an arrow A12, a surgical instrument is inserted through the incision 103 into the anterior capsule incision part of the eye lens 104, emulsification (pulverization) and aspiration of the nucleus of the eye lens 104 by ultrasonic vibration called nucleus treatment are performed, and the cortex is also aspirated. Then, an intraocular lens 105 is inserted inside the eye lens 104 as shown by an arrow A13, and the surgery is completed.

In the cataract surgery as described above, examples of a dangerous condition to be detected include, for example, items listed below.

(1) Shallow anterior chamber: condition of anterior chamber having narrow space between posterior corneal surface and anterior iris surface
(2) Infusion misdirection syndrome (IMS) risk: flowing of surgery irrigation fluid into posterior side of eye lens
(3) Posterior capsule rupture: condition where posterior capsule that is posterior part of eye lens is damaged
(4) Nucleus drop: nucleus of eye lens drops from ruptured part at occurrence of posterior capsule rupture
(5) Implant misplacement: insertion of implant (object embedded in body) at an abnormal position
(6) Iris prolapse risk: protrusion of iris out of the eye through incision The above-described items (1) to (6) include a case of detecting occurrence of a dangerous condition such as posterior capsule rupture and implant misplacement and a case of detecting a condition in which occurrence of a dangerous condition such as an iris prolapse risk and IMS risk is expected. However, herein, both the cases described above are considered to be defined as a dangerous condition.

<2. Block Diagram Related to Detection and Reporting of Dangerous Condition>

Figure 4:
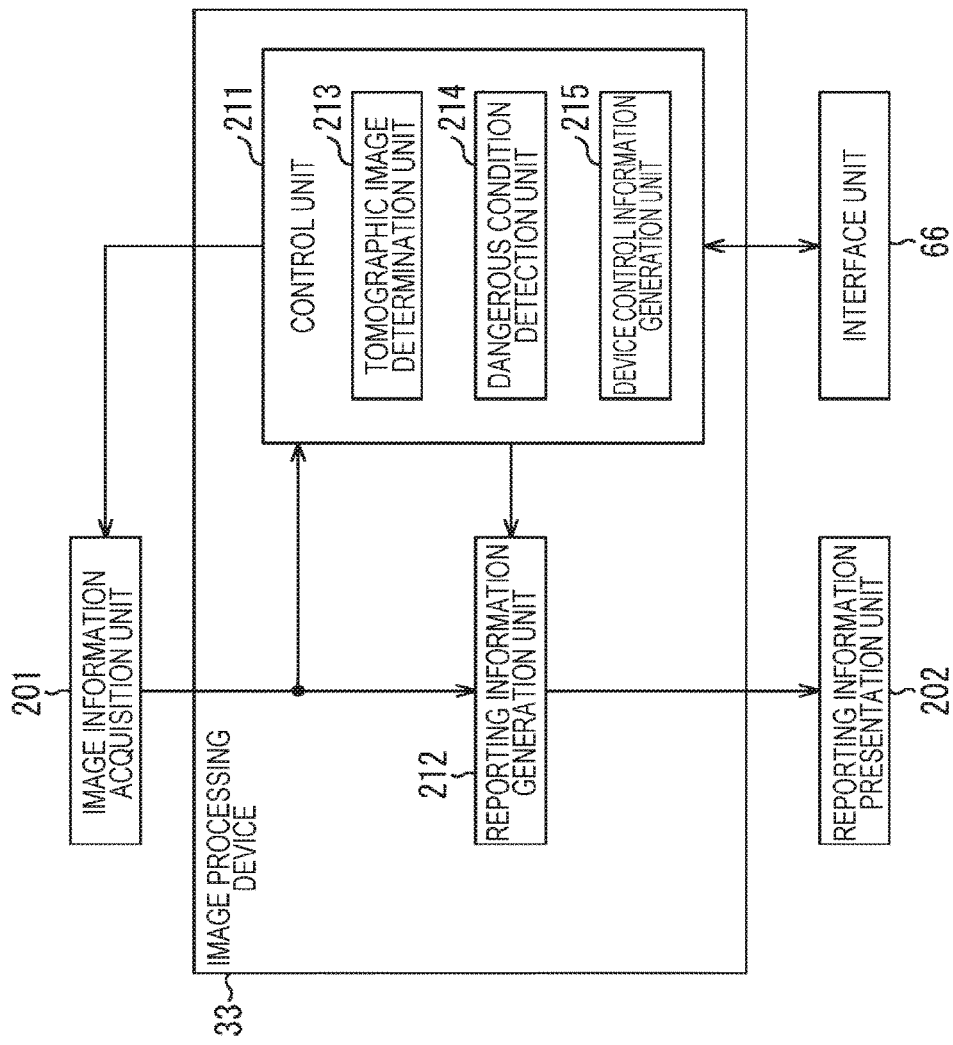
FIG. 4 is a block diagram illustrating a component related to detection and reporting of a dangerous condition.

FIG. 4 is a block diagram illustrating a component related to detection and reporting of a dangerous condition in the surgical system 11. In FIG. 4, portions corresponding to those in FIGS. 1 and 2 are denoted with the same reference signs, and the description thereof is omitted as appropriate.

The surgery system 11 relates to the detection and reporting of a dangerous condition, and is configured to include an image information acquisition unit 201, the image processing device 33, a reporting information presentation unit 202, and the interface unit 66. In addition, the image processing device 33 is configured to include a control unit 211 and a reporting information generation unit 212.

Figure 5:
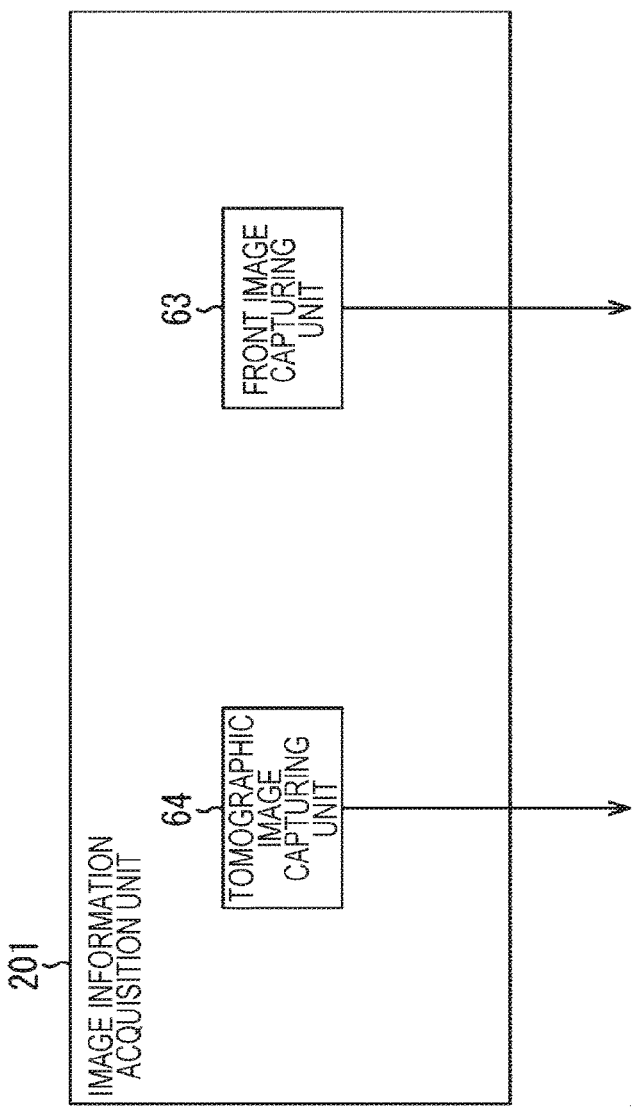
FIG. 5 is a block diagram illustrating a configuration example of an image information acquisition unit.

The image information acquisition unit 201 acquires a tomographic image or a front image and supplies the acquired image to the image processing device 33 under the control of the control unit 211 of the image processing device 33. Specifically, the image information acquisition unit 201 corresponds to the front image capturing unit 63 and the tomographic image capturing unit 64 as illustrated in FIG. 5. The front image capturing unit 63 captures the front image and supplies it to the control unit 211 and the reporting information generation unit 212. The tomographic image capturing unit 64 captures the tomographic image and supplies it to the control unit 211 and the reporting information generation unit 212. A method of acquiring the tomographic image is determined by the control unit 211 on the basis of a recognition result or other information of the front image, and is instructed to the tomographic image capturing unit 64.

The control unit 211 of the image processing device 33 controls the overall operation of the surgical microscope 21, for example, such as a change of the illumination condition of the light source 61 and a change of the zoom magnification of the observation optical system 62.

Further, the control unit 211 relates to the detection and reporting of a dangerous condition, and is configured to include a tomographic image determination unit 213, a dangerous condition detection unit 214, and a device control information generation unit 215.

The tomographic image determination unit 213 determines a capture plane (tomographic plane) to be captured by the tomographic image capturing unit 64 on the basis of the front image or the like supplied from the image information acquisition unit 201, and designates it to the tomographic image capturing unit 64. In one example, the tomographic image determination unit 213 recognizes the front image to detect the range of the cornea of the eye, the range of the pupil, and the like, and determines the plane passing through the center position of the cornea as the tomographic plane. A method of determining the tomographic plane differs depending on the dangerous condition to be detected, and thus detailed description thereof will be given later.

The dangerous condition detection unit 214 detects the dangerous condition during the eye surgery on the basis of the tomographic image supplied from the image information acquisition unit 201. The dangerous condition detection unit 214 may calculate a predetermined risk parameter from the tomographic image and may detect the dangerous condition on the basis of the calculated risk parameter, or may detect the dangerous condition directly from the tomographic image.

When the dangerous condition is detected, the dangerous condition detection unit 214 instructs the reporting information generation unit 212 to generate reporting information used to report the dangerous condition to the surgeon or other specialists.

When the dangerous condition is detected, the device control information generation unit 215 generates device control information used to control the external device and supplies it to the interface unit 66. In one example, the device control information generation unit 215 sets the risk parameter calculated by the dangerous condition detection unit 214 as the device control information and supplies it to the external device through the interface unit 66. In addition, in one example, the device control information generation unit 215 supplies, as the device control information, a device control signal used to stop the operation of an ultrasonic phacoemulsification instrument 261 (FIG. 10) that is an external device to the external device through the interface unit 66.

When the dangerous condition is detected, the reporting information generation unit 212 generates reporting information used to report the dangerous condition to the surgeon or other specialists under the control of the control unit 211, and supplies the reporting information to the reporting information presentation unit 202. The reporting information is, for example, a sound control signal used to output sound such as buzzer sound or melody sound, a screen control signal of a screen used to report the detection of a dangerous condition, or the like. In addition, the front image or the tomographic image itself may be supplied to the reporting information presentation unit 202 as the reporting information.

The device control information generation unit 215 and the reporting information generation unit 212 correspond to a control information generation unit that generates and outputs control information used to manage the detected dangerous condition.

The reporting information presentation unit 202 presents the reporting information supplied from the reporting information generation unit 212 to the surgeon. The reporting information presentation unit 202 corresponds to a rotary lamp or indicator light (lamp) such as the monitor 34 or the loudspeaker 67.

<3. Processing Procedure of Dangerous Condition Detection and Reporting Processing>

Figure 6:
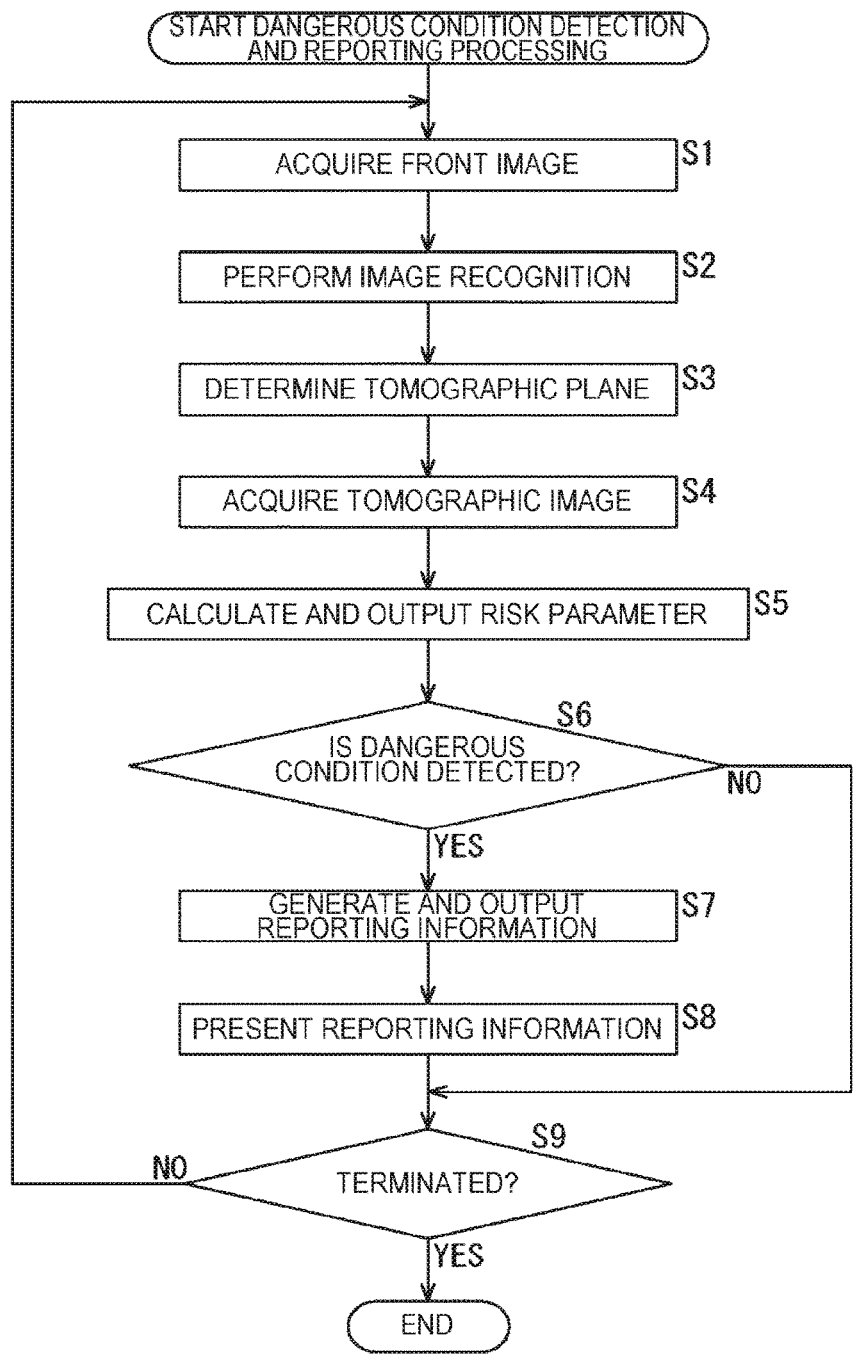
FIG. 6 is a flowchart illustrated to describe dangerous condition detection and reporting processing performed by a surgical microscope.

With reference to the flowchart of FIG. 6, dangerous condition detection and reporting processing performed by the surgical microscope 21 as processing that is common to the dangerous conditions of the above-described items (1) to (6) is described.

In step S1, the image information acquisition unit 201 acquires the front image of the eye and supplies it to the control unit 211.

Figure 7:
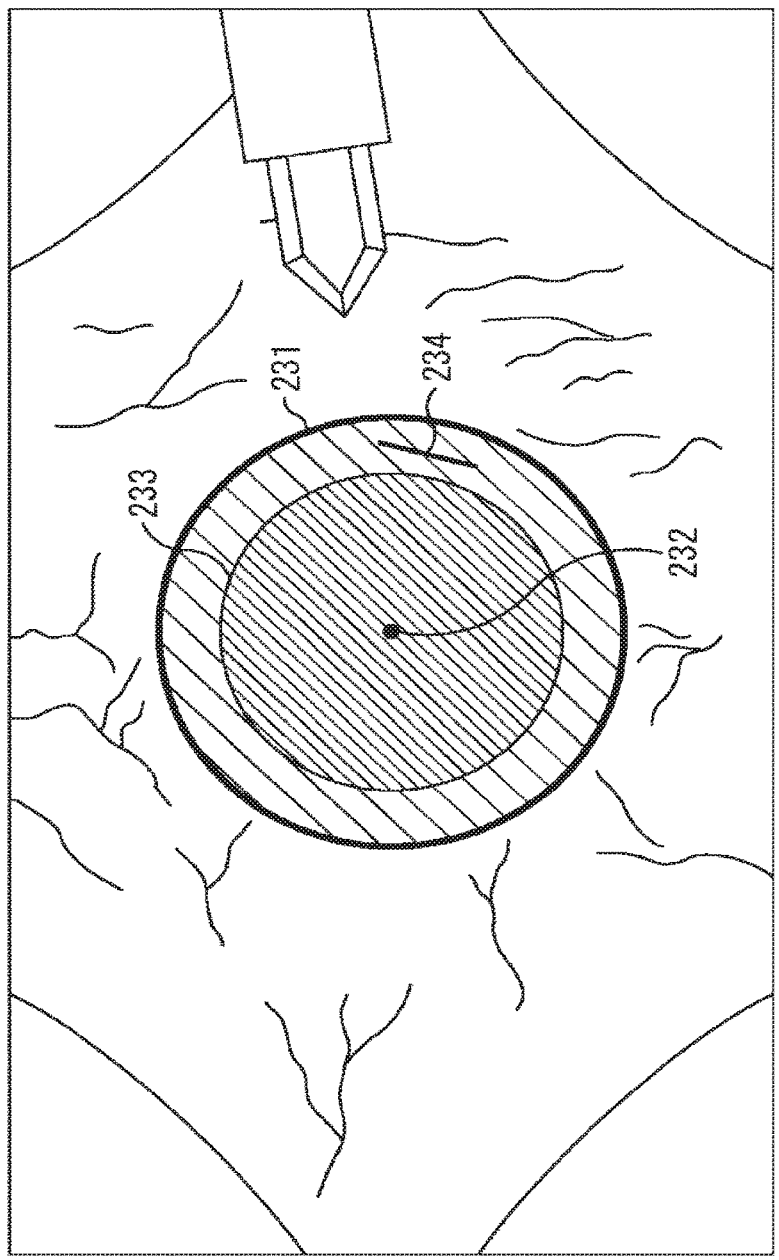
FIG. 7 is a diagram illustrated to describe image recognition processing on a front image.

In step S2, the tomographic image determination unit 213 of the control unit 211 performs image recognition processing on the front image of the eye supplied from the image information acquisition unit 201. In the image recognition processing on the front image, for example, a predetermined position of the eye, which is necessary to determine the tomographic plane, such as the center position 232 of the cornea (corneal limbus) 231 of the eye illustrated in FIG. 7, is detected. FIG. 7 is a conceptual diagram of a front image obtained by capturing the eye of a patient opened with an eyelid retractor from the front. In FIG. 7, the pupil 233 is inside the cornea 231, and a position 234 of the incision is in the region of the cornea 231 outside the pupil 233.

In step S3, the tomographic image determination unit 213 of the control unit 211 determines a tomographic plane that is a plane in which a tomographic image is acquired, on the basis of a result obtained by performing image recognition on the front image. The control unit 211 supplies information used to specify the determined tomographic plane (tomographic plane specifying information) to the image information acquisition unit 201.

In step S4, the image information acquisition unit 201 acquires a tomographic image on the basis of the tomographic plane specifying information supplied from the control unit 211, and supplies the tomographic image to the control unit 211 and the reporting information generation unit 212. The tomographic image is acquired continuously at a predetermined frame rate (e.g., 30 images per second).

In step S5, the dangerous condition detection unit 214 of the control unit 211 calculates and outputs a risk parameter on the basis of the tomographic image supplied from the image information acquisition unit 201. Moreover, calculation and output of a risk parameter may be omitted depending on the dangerous condition to be detected. In the case where the risk parameter is output, the calculated risk parameter is supplied to the interface unit 66 through the device control information generation unit 215 and is output from the interface unit 66 to the external device.

In step S6, the dangerous condition detection unit 214 determines whether the dangerous condition to be detected is detected on the basis of the calculated risk parameter. In addition, in the case where the calculation of the risk parameter is omitted, the dangerous condition detection unit 214 determines whether the dangerous condition to be detected is detected on the basis of the tomographic image supplied from the image information acquisition unit 201.

If it is determined in step S6 that the dangerous condition to be detected is detected, the processing proceeds to step S7, and the processing procedures in steps S7 and S8, which will be described later, are executed. On the other hand, if it is determined in step S6 that no dangerous condition is detected, the processing procedures in steps S7 and S8 are skipped, and the processing proceeds to step S9.

If it is determined in step S6 that the dangerous condition to be detected is detected, the processing proceeds to step S7, and the reporting information generation unit 212 generates and outputs the reporting information under the control of the control unit 211.

More specifically, in step S7, in one example, the dangerous condition detection unit 214 of the control unit 211 instructs the reporting information generation unit 212 to output buzzer sound as the reporting information. In addition, the dangerous condition detection unit 214 instructs the reporting information generation unit 212 to set the tomographic image supplied from the image information acquisition unit 201 as the reporting information. Under the control of the control unit 211, the reporting information generation unit 212 outputs a control signal used to control the loudspeaker 67 (acoustic signal) to the reporting information presentation unit 202, and supplies the tomographic image supplied from the image information acquisition unit 201 to the reporting information presentation unit 202 as the reporting information.

Further, in the case of controlling the external device depending on the detected dangerous condition, the device control information generation unit 215 of the control unit 211 in step S7 supplies the device control information used to control the external device to the interface unit 66.

In step S8, the reporting information presentation unit 202 presents the reporting information on the basis of the reporting information supplied from the reporting information generation unit 212. In one example, the loudspeaker 67 serving as the reporting information presentation unit 202 outputs buzzer sound. The monitor 34 serving as the reporting information presentation unit 202 displays the tomographic image supplied from the reporting information generation unit 212.

Moreover, instead of simultaneously outputting the buzzer sound and displaying the tomographic image, in one example, the reporting information presentation unit 202 outputs buzzer sound, and then, in the case where an surgeon who recognizes the dangerous condition on the basis of the buzzer sound instructs the reporting information presentation unit 202 to display the tomographic image through the interface unit 66, the reporting information presentation unit 202 may present (display) the tomographic image.

In step S9, the control unit 211 determines whether to terminate the dangerous condition detection and reporting processing. In one example, in the case where the surgeon instructs to stop the processing by an operation of the touch panel or the like after the reporting information is presented in step S8, the control unit 211 determines to terminate the dangerous condition detection and reporting processing.

If it is determined in step S9 not to terminate the dangerous condition detection and reporting processing yet, the processing returns to step S1 and the subsequent processing procedures are repeatedly executed.

On the other hand, if it is determined in step S9 to terminate the dangerous condition detection and reporting processing, the processing ends.

The dangerous condition detection and reporting processing executed as described above makes it possible, during the eye surgery, to detect the dangerous condition on the basis of the tomographic image and to report it to the surgeon. In addition, it is possible to control the external device (automatically) without the surgeon's operation.

Next, for each case of the above-described six types of dangerous conditions in cataract surgery, that is, (1) shallow anterior chamber, (2) MIS risk, (3) posterior capsule rupture, (4) nucleus drop, (5) implant misplacement, and (6) iris prolapse risk, portions different from the dangerous condition detection and reporting processing described with reference to FIG. 6 are described in detail. Moreover, in the description of each of the dangerous conditions, each step of the dangerous condition detection and reporting processing illustrated in FIG. 6 is cited as appropriate.

<4. Detection Example of Shallow Anterior Chamber>

Detection of shallow anterior chamber of the item (1) is described.

Figure 8:
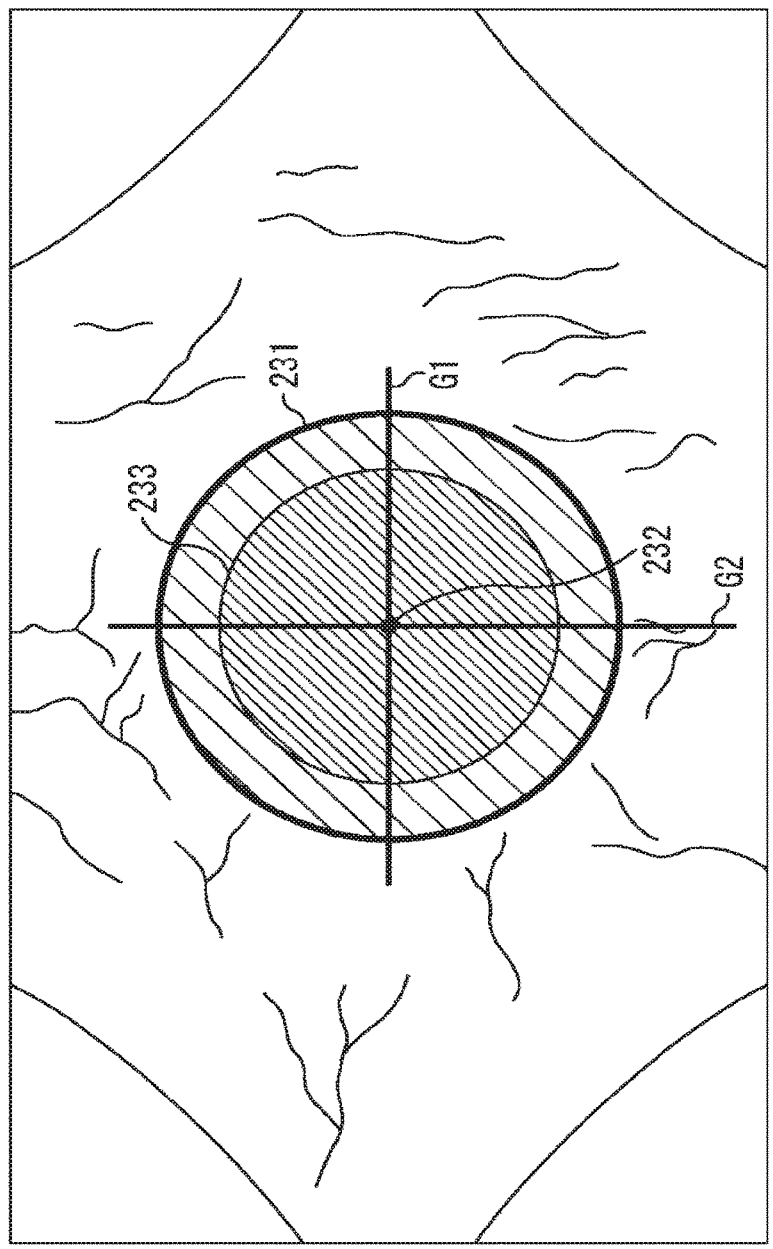
FIG. 8 is a diagram illustrated to describe determination of a tomographic plane in detecting a shallow anterior chamber.

In the detection of the shallow anterior chamber, in step S3, as illustrated in FIG. 8, the control unit 211 determines planes G1 and G2 as the tomographic plane. The planes G1 and G2 passing through the center position 232 of the cornea 231 recognized from the front image are respectively parallel to the horizontal direction and the vertical direction of the front image. Then, the control unit 211 generates tomographic plane specifying information used to specify the determined tomographic plane and supplies it to the image information acquisition unit 201.

In step S4, the image information acquisition unit 201 acquires a tomographic image on the basis of the tomographic plane specifying information supplied from the control unit 211, and supplies the tomographic image to the control unit 211.

Figure 9:
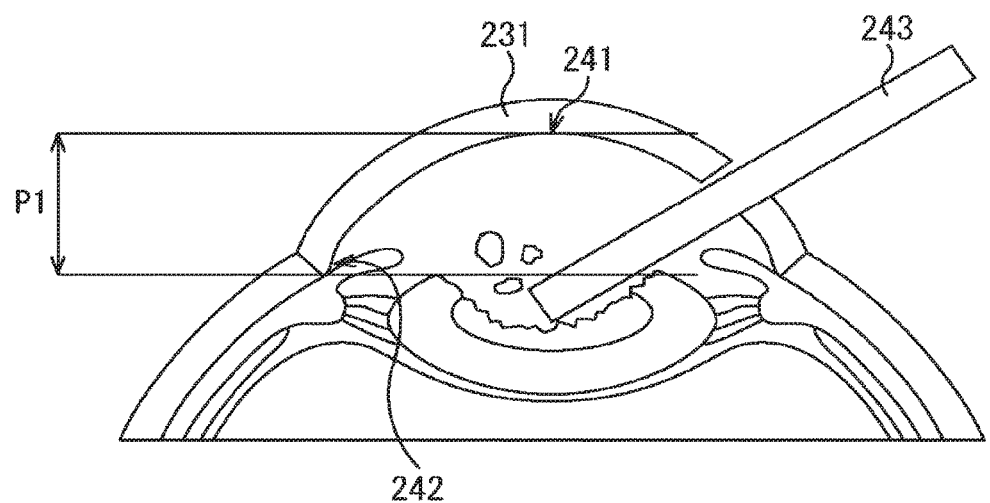
FIG. 9 is a diagram illustrated to describe a risk parameter in detecting a shallow anterior chamber.

In step S5, the control unit 211 calculates, as a risk parameter, a distance P1 from the corneal vertex 241 to the iridocorneal angle 242 (e.g., a distance in perpendicular direction), as illustrated in FIG. 9, on the basis of the tomographic image supplied from the image information acquisition unit 201. Moreover, in FIG. 9, the corneal vertex 241 is on the bottom side of the cornea 231, but it may be on the upper side of the cornea 231. In addition, the normalized value obtained by dividing the distance P1 from the corneal vertex 241 to the iridocorneal angle 242 by the corneal radius may be used as the risk parameter.

Figure 10:
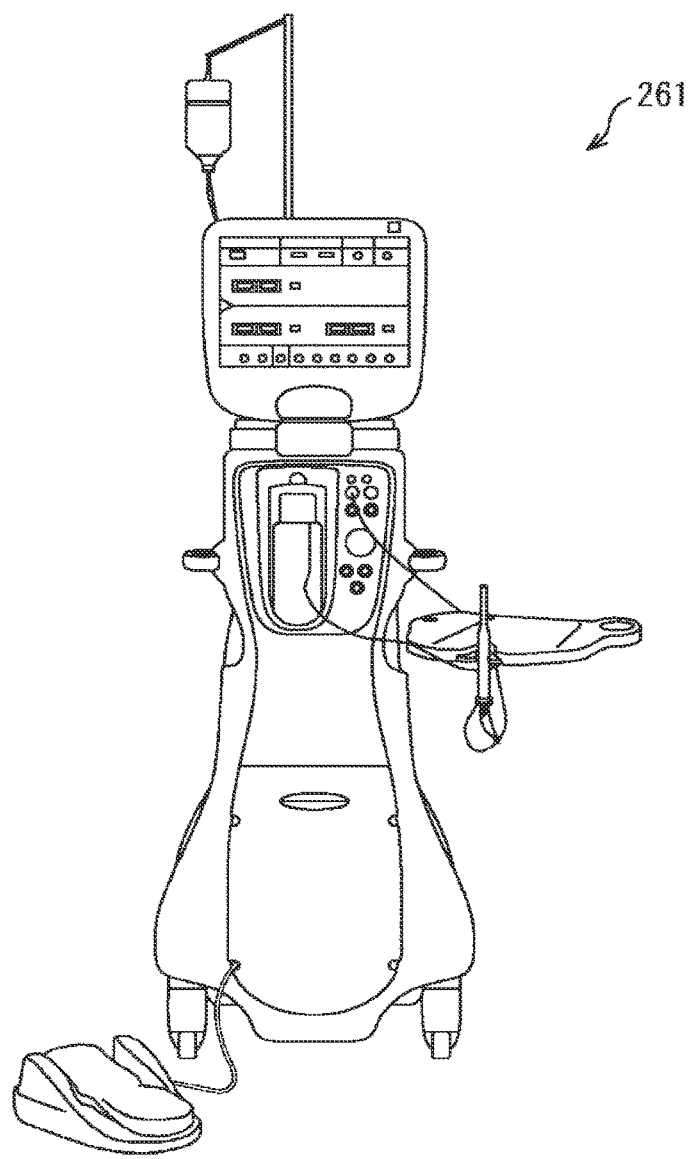
FIG. 10 is a diagram illustrating an ultrasonic phacoemulsification instrument as an external device.

Further, in step S5, the calculated risk parameter is output, as device control information used to control the external device, to the ultrasonic phacoemulsification instrument 261 illustrated in FIG. 10 through the interface unit 66. The ultrasonic phacoemulsification instrument 261 regulates the pressure of the irrigation fluid (irrigation pressure) on the basis of the supplied risk parameter. More specifically, the ultrasonic phacoemulsification instrument 261 regulates the irrigation pressure so that the irrigation pressure increases as the risk parameter becomes smaller than a predetermined value. The irrigation pressure can be regulated, for example, by adjusting the height of the irrigation fluid bottle.

In step S6, the control unit 211 determines whether the dangerous condition, that is, the shallow anterior chamber is detected on the basis of whether the distance P1 from the corneal vertex 241 to the iridocorneal angle 242 as the risk parameter is smaller than a preset threshold.

If it is determined in step S6 that the shallow anterior chamber is detected, the reporting information generation unit 212, in step S7, generates reporting information and supplies the reporting information to the reporting information presentation unit 202 under control of the control unit 211.

In step S8, the loudspeaker 67 serving as the reporting information presentation unit 202 outputs buzzer sound. The monitor 34 serving as the reporting information presentation unit 202 displays the tomographic image supplied from the reporting information generation unit 212. Moreover, the tomographic image may be displayed after the surgeon's operation to display the tomographic image as described above.

Figure 11:
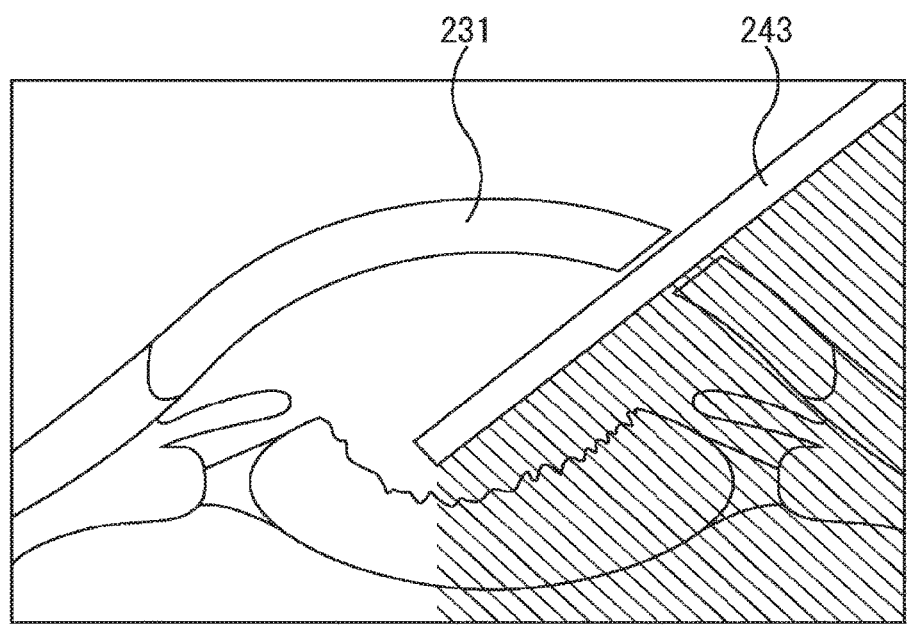
FIG. 11 is a diagram illustrating an example of a tomographic image in detecting a shallow anterior chamber.

FIG. 11 illustrates an example of the tomographic image displayed on the monitor 34 as the reporting information. In the tomographic image, the lower side of a surgical tool 243 is shadowed because the tomographic information fails to be acquired from that region.

The dangerous situation detection informing process for detecting the shallow anterior chamber and reporting it to the surgeon as described above makes it possible to detect and quickly manage the condition where complications such as iris damage or corneal endothelial cell disorder are likely to occur, thereby preventing the occurrence of complications. In addition, the distance P1 from the corneal vertex 241 to the iridocorneal angle 242, which is a risk parameter, is output to the external device as the device control information, so this can contribute to the prevention of complications.

<5. Detection Example of IMS Risk>

Next, detection of IMS risk of the item (2) is described.

In the detection of the IMS risk, in step S3 of the dangerous condition detection and reporting processing, as illustrated in FIG. 8, the control unit 211 determines the planes G1 and G2 as the tomographic plane. The planes G1 and G2 pass through the center position 232 of the cornea 231 recognized from the front image and they are respectively parallel to the horizontal direction and the vertical direction of the front image. Then, the control unit 211 generates tomographic plane specifying information used to specify the determined tomographic plane and supplies it to the image information acquisition unit 201.

In step S4, the image information acquisition unit 201 acquires a tomographic image on the basis of the tomographic plane specifying information supplied from the control unit 211, and supplies the tomographic image to the control unit 211.

Figure 12:
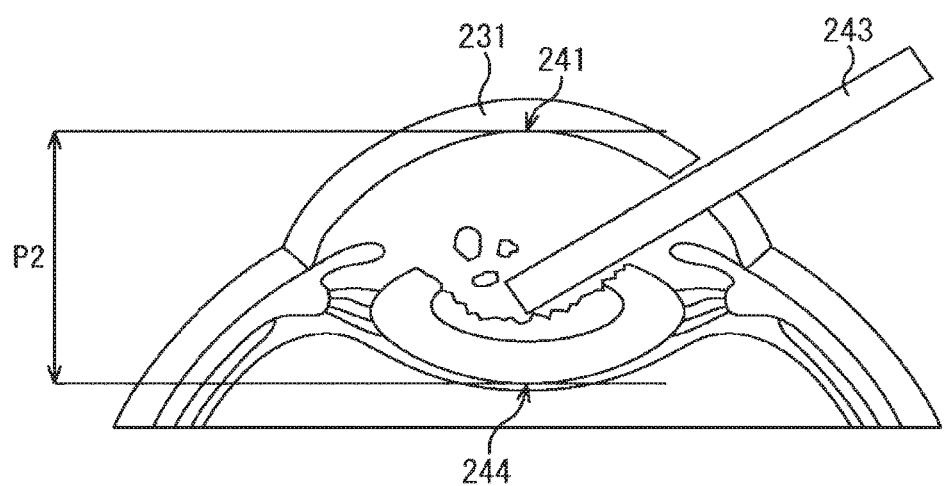
FIG. 12 is a diagram illustrated to describe a risk parameter in detecting an IMS risk.

In step S5, the control unit 211 calculates, as a risk parameter, a distance P2 from the corneal vertex 241 to a lower end 244 of the posterior capsule (e.g., a distance in perpendicular direction), as illustrated in FIG. 12, on the basis of the tomographic image supplied from the image information acquisition unit 201. Moreover, in FIG. 9, the corneal vertex 241 is on the bottom side of the cornea 231, but it may be on the upper side of the cornea 231. In addition, the normalized value obtained by dividing the distance P2 from the corneal vertex 241 to the lower end 244 of the posterior capsule by the corneal radius may be used as the risk parameter.

Further, in step S5, the calculated risk parameter is output as the device control information to the ultrasonic phacoemulsification instrument 261 illustrated in FIG. 10 through the interface unit 66. The ultrasonic phacoemulsification instrument 261 regulates the pressure of the irrigation fluid (irrigation pressure) on the basis of the supplied risk parameter. More specifically, the ultrasonic phacoemulsification instrument 261 regulates the irrigation pressure so that the irrigation pressure decreases as the risk parameter becomes larger than a predetermined value. The irrigation pressure can be regulated, for example, by adjusting the height of the irrigation fluid bottle.

In step S6, the control unit 211 determines whether the dangerous condition, that is, the IMS risk is detected on the basis of whether the distance P2 from the corneal vertex 241 to the lower end 244 of the posterior capsule as the risk parameter is larger than a preset threshold.

If it is determined in step S6 that the IMS risk is detected, the reporting information generation unit 212, in step S7, generates reporting information and supplies the reporting information to the reporting information presentation unit 202 under control of the control unit 211.

In step S8, the loudspeaker 67 serving as the reporting information presentation unit 202 outputs buzzer sound. The monitor 34 serving as the reporting information presentation unit 202 displays the tomographic image supplied from the reporting information generation unit 212. Moreover, the tomographic image may be displayed after the surgeon's operation to display the tomographic image as described above.

Figure 13:
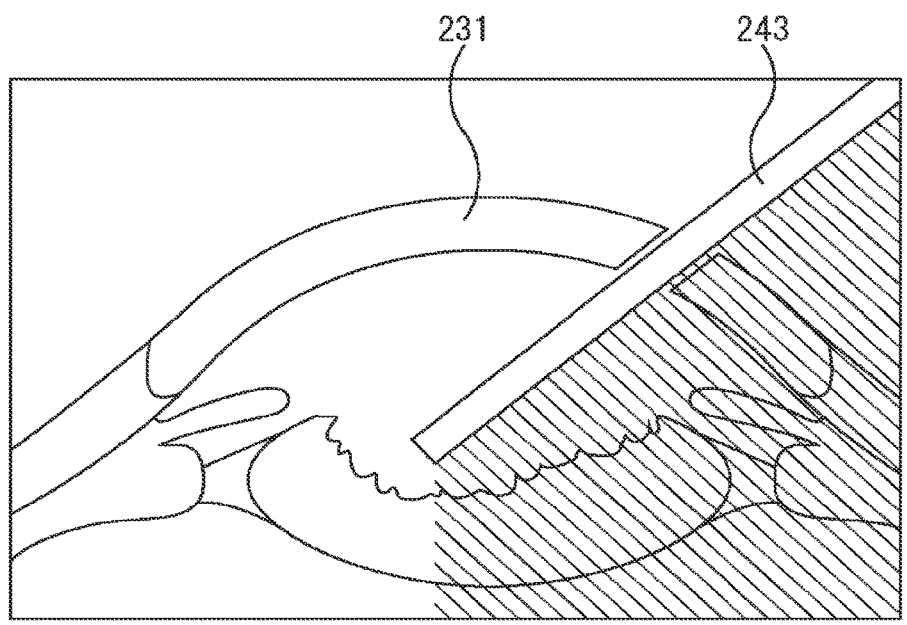
FIG. 13 is a diagram illustrating an example of a tomographic image in detecting an IMS risk.

FIG. 13 illustrates an example of the tomographic image displayed on the monitor 34 as the reporting information. In the tomographic image, the lower side of the surgical tool 243 is shadowed because the tomographic information fails to be acquired from that region.

The dangerous condition detection and reporting processing for detecting the IMS risk and reporting it to the surgeon as described above makes it possible to detect and quickly manage the condition where IMS, which is a complication, is likely to occur, thereby preventing the occurrence of complications. In addition, the distance P2 from the corneal vertex 241 to the lower end 244 of the posterior capsule, which is a risk parameter, is output to the external device as the device control information, so this can contribute to the prevention of complications.

<6. Detection Example of Posterior Capsule Rupture>

Next, detection of posterior capsule rupture of the item (3) is described.

Figure 14:
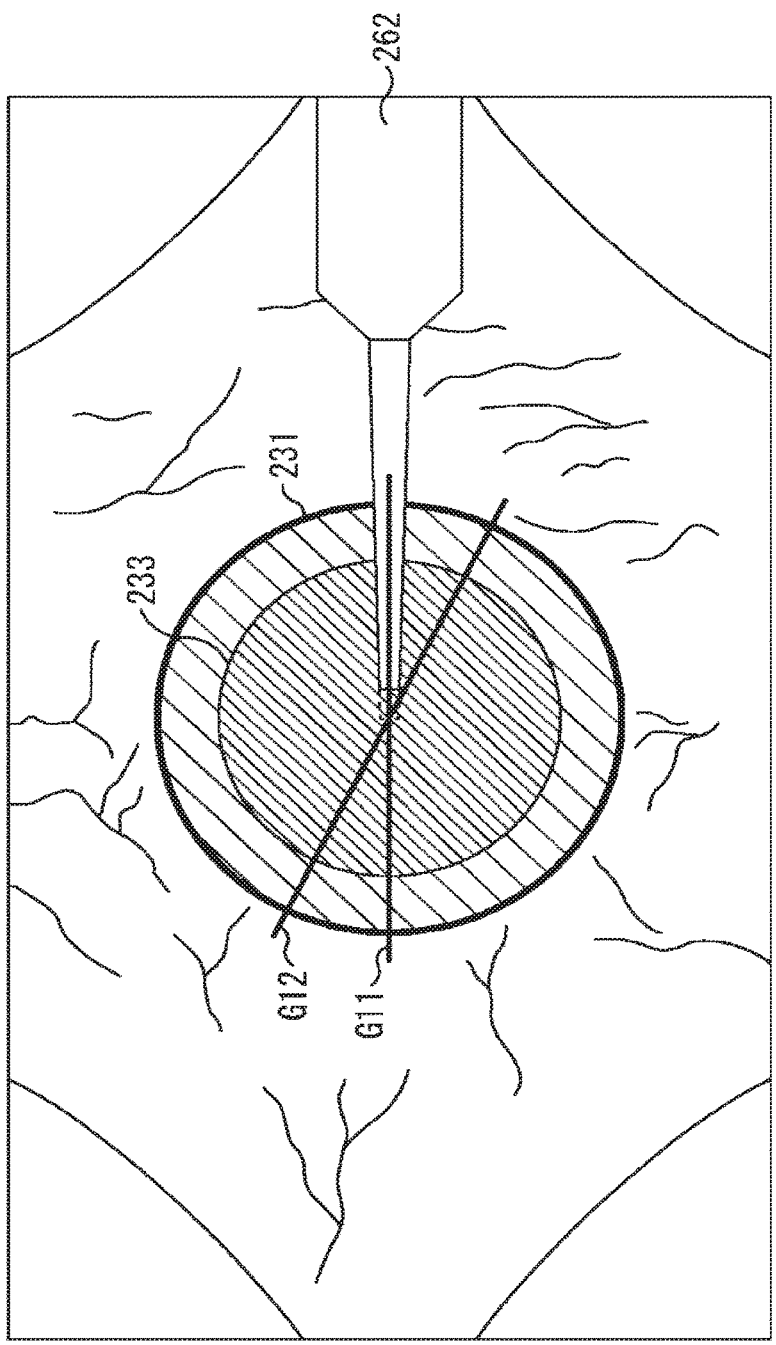
FIG. 14 is a diagram illustrated to describe determination of a tomographic plane in detecting posterior capsule rupture.

In the detection of the posterior capsule rupture, in step S3 of the dangerous condition detection and reporting processing, as illustrated in FIG. 14, the control unit 211 determines planes G11 and G12 as the tomographic plane. The plane G11 passes through the tip of a surgical tool 262 recognized from the front image, and the plane G11 is parallel to the longitudinal direction of the surgical tool 262. The plane G12 is displaced (rotated) by a predetermined angle around the tip of the surgical tool 262 relative to the plane G11. Then, the control unit 211 generates tomographic plane specifying information used to specify the determined tomographic plane and supplies it to the image information acquisition unit 201. Moreover, the intersection angle between the planes G11 and G12 is optional, and may be, for example, an orthogonal angle.

In step S4, the image information acquisition unit 201 acquires a tomographic image on the basis of the tomographic plane specifying information supplied from the control unit 211, and supplies the tomographic image to the control unit 211.

Figure 15:
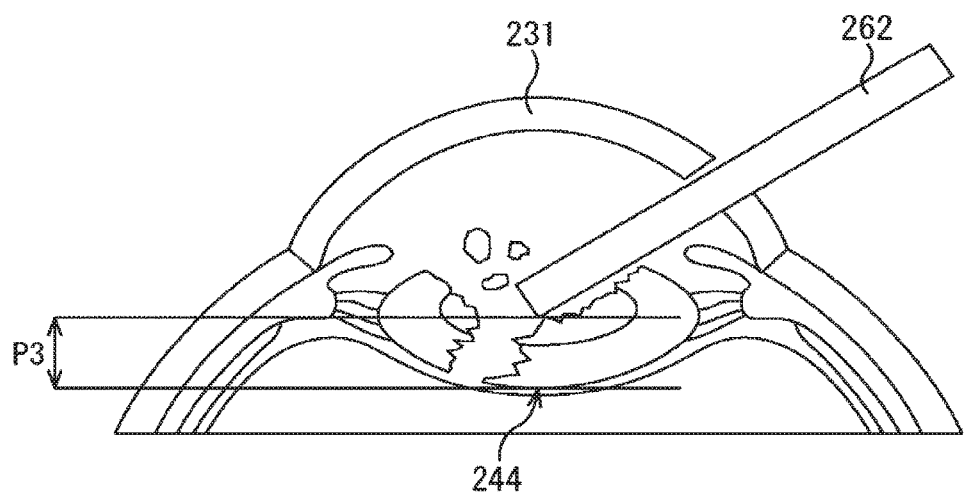
FIG. 15 is a diagram illustrated to describe a risk parameter in detecting posterior capsule rupture.

In step S5, the control unit 211 calculates, as a risk parameter, a distance P3 from the tip of the surgical tool 262 to the lower end 244 of the posterior capsule (e.g., a distance in perpendicular direction), as illustrated in FIG. 15, on the basis of the tomographic image supplied from the image information acquisition unit 201.

In the next step S6, it is determined whether the posterior capsule rupture is detected on the basis of the acquired tomographic image. However, the processing procedures from step S1 to step S9 (case of being determined as NO in step S6) are repeated until the distance P3 from the tip of the surgical tool 262 to the lower end 244 of the posterior capsule, which is the risk parameter, reaches a small value to some extent.

Figure 16:
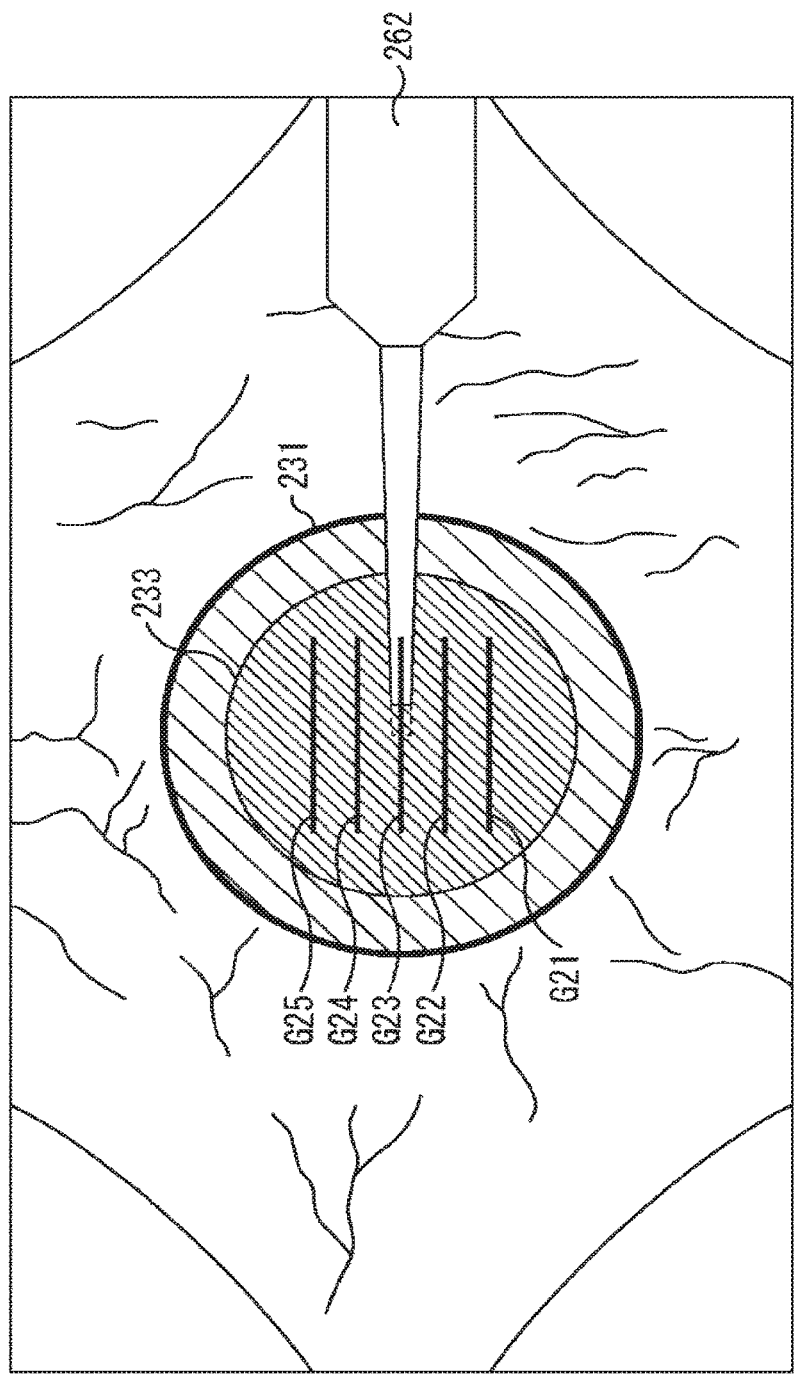
FIG. 16 is a diagram illustrated to describe a risk parameter in detecting posterior capsule rupture.

Then, when the risk parameter becomes a value smaller than a predetermined value and the distance from the tip of the surgical tool 262 to the lower end 244 of the posterior capsule comes close to predetermined proximity, the control unit 211 determines a plurality of planes G21 to G25 as the tomographic plane in step S3, as illustrated in FIG. 16. The plurality of planes G21 to G25 are planes obtained by equally dividing a predetermined three-dimensional space composed of the tomographic direction and the horizontal and vertical directions (hereinafter referred to as tomographic capturing space) on the plurality of tomographic planes with the tip of the surgical tool 262 being the center in the plane direction.

Figure 17:
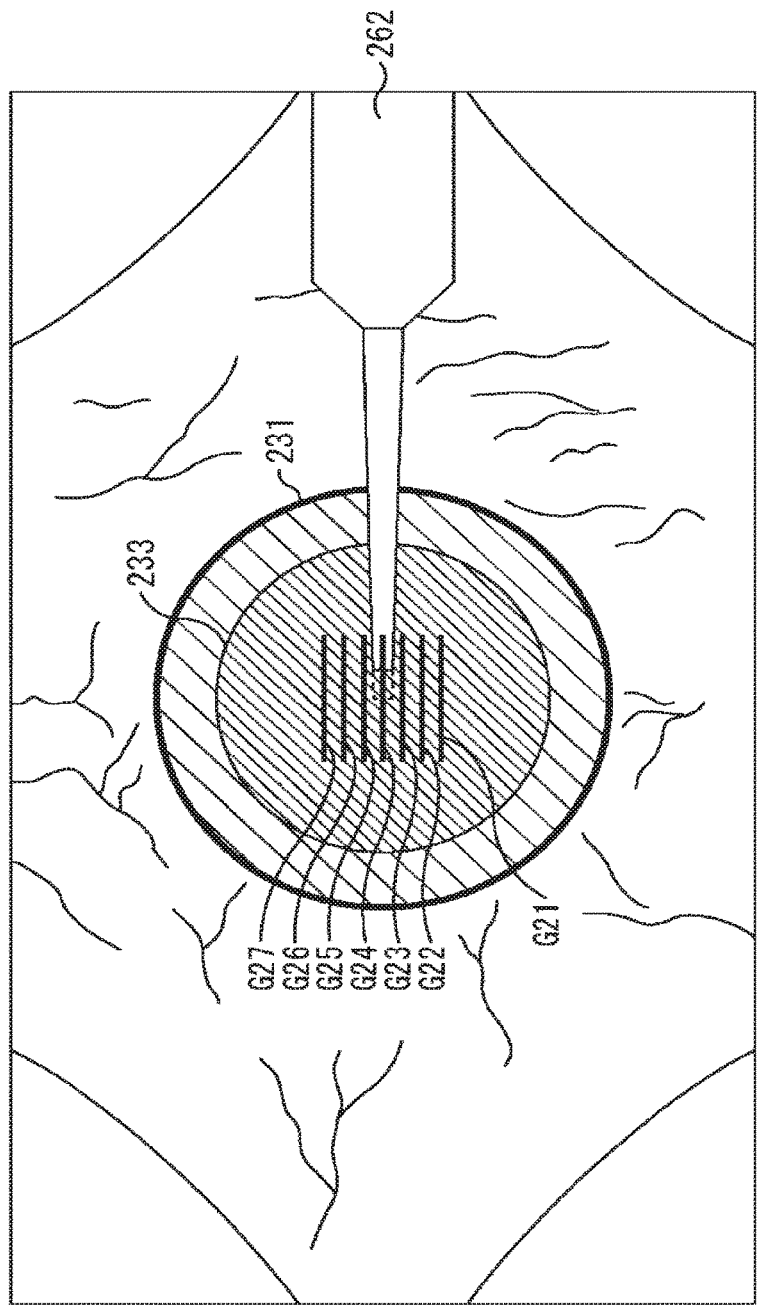
FIG. 17 is a diagram illustrated to describe a risk parameter in detecting posterior capsule rupture.

When the distance from the tip of the surgical tool 262 to the lower end 244 of the posterior capsule further decreases, the control unit 211 sets the tomographic capturing space to be further smaller, and determines the tomographic plane so that the number and the density of tomographic images increase in step S3, as illustrated in FIG. 17. The tomographic capturing space in the example of FIG. 17 is set to be smaller than that in the case of FIG. 16, and, as the number of the tomographic planes, seven planes, i.e., planes G21 to G27, which are two more than the five planes G21 to G25 in FIG. 16, are determined as the tomographic planes.

As described above, in detecting the posterior capsule rupture, a tomographic plane to be captured is also dynamically determined (changed) depending on the risk parameter that varies during the surgery.

Figure 18:
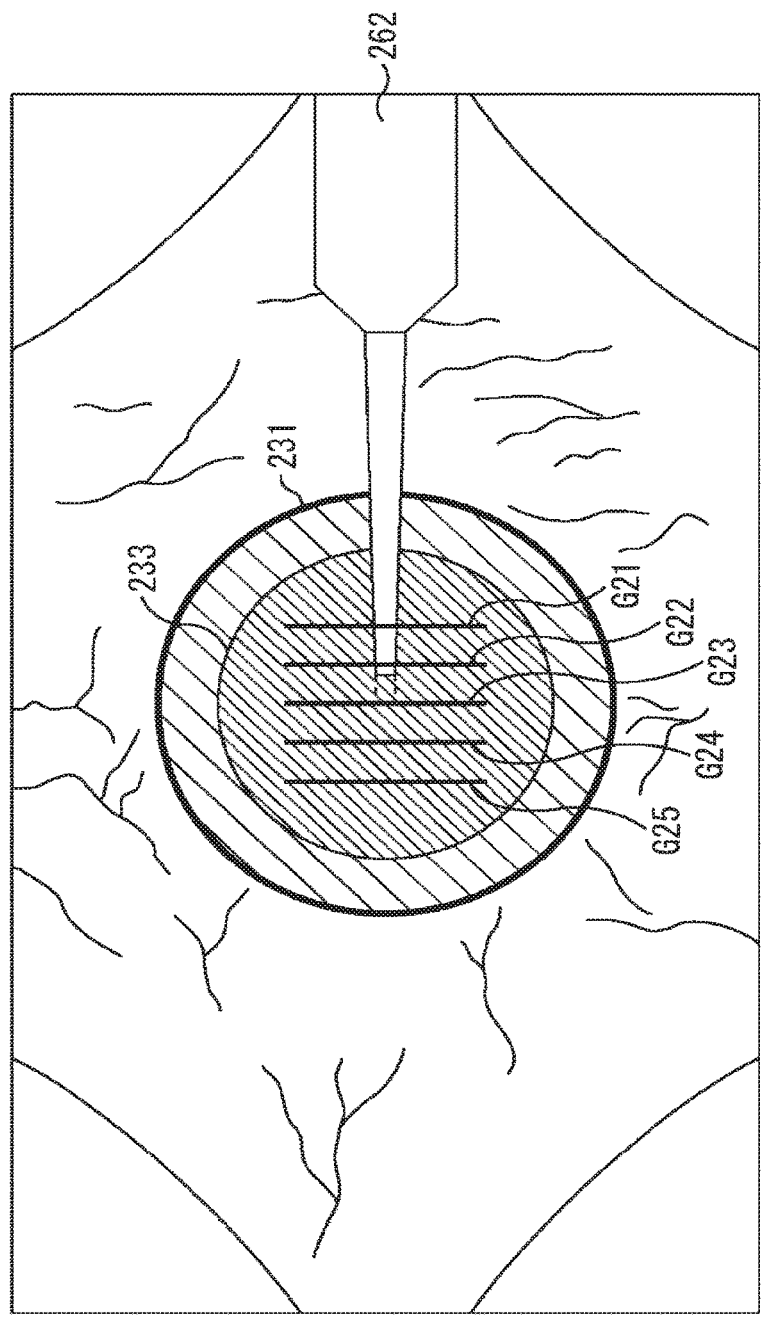
FIG. 18 is a diagram illustrated to describe a risk parameter in detecting posterior capsule rupture.
Figure 19:
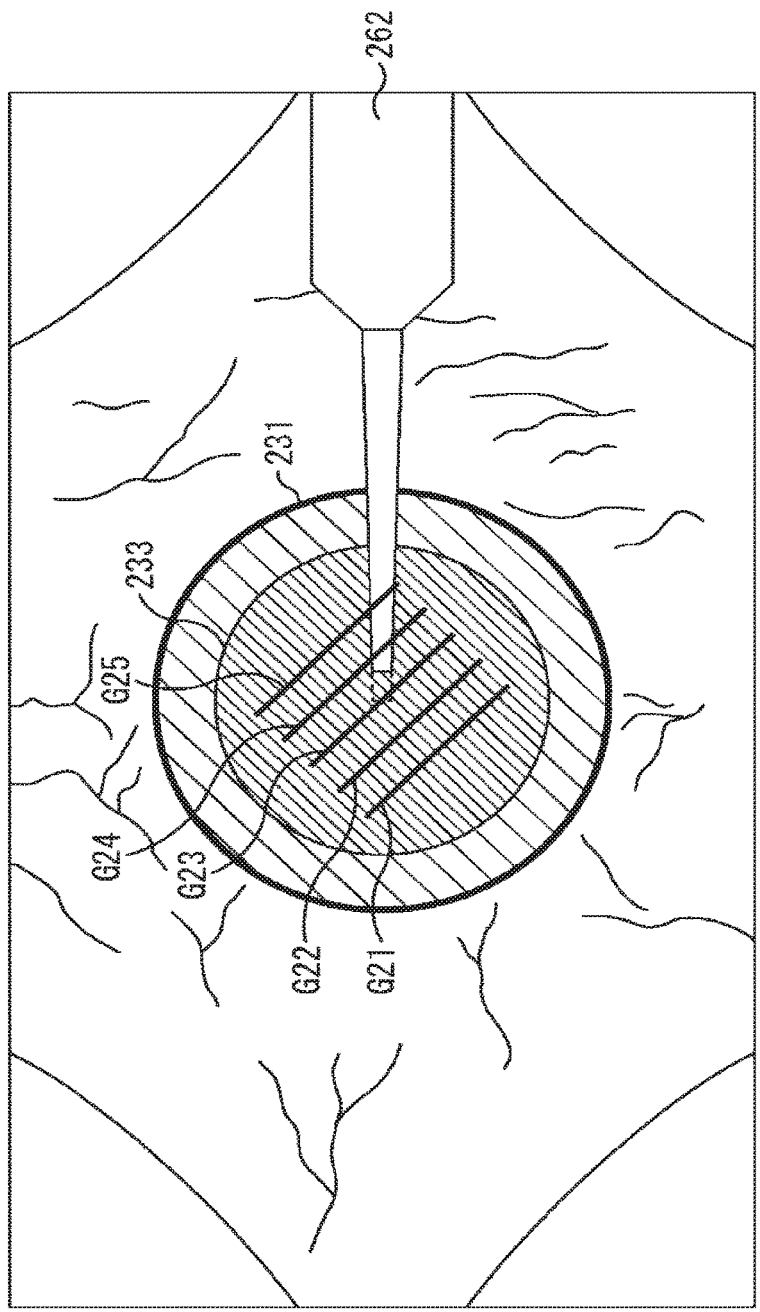
FIG. 19 is a diagram illustrated to describe a risk parameter in detecting posterior capsule rupture.
Figure 20:
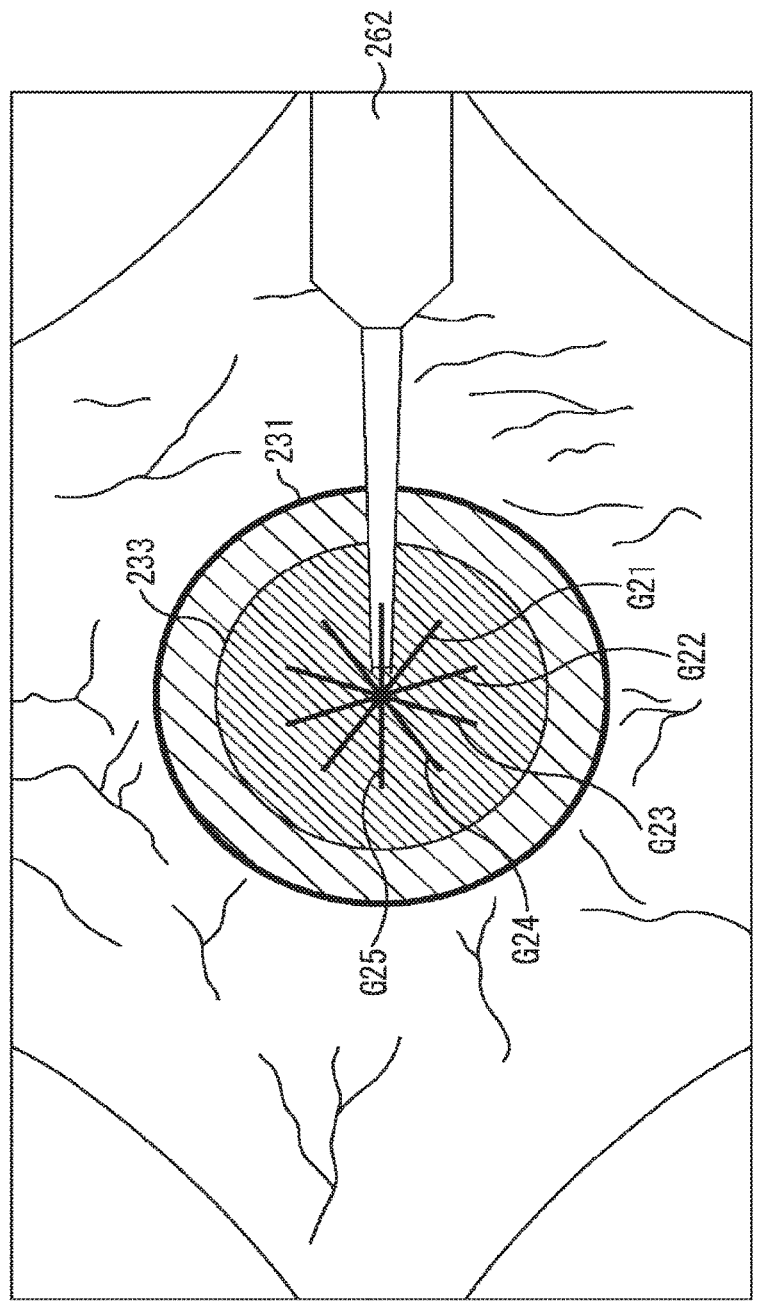
FIG. 20 is a diagram illustrated to describe a risk parameter in detecting posterior capsule rupture.

Moreover, the positions of a plurality of tomographic planes can be determined so that the tomographic planes may cover the tomographic capturing space. Thus, the plurality of tomographic planes are not limited to the planes parallel to the longitudinal direction of the surgical instrument 262 as illustrated in FIGS. 16 and 17. In one example, as the tomographic planes, a plurality of planes G21 to G25 perpendicular to the longitudinal direction of the surgical tool 262 as illustrated in FIG. 18, a plurality of planes G21 to G25 having a predetermined angle in the longitudinal direction of the surgical tool 262 as illustrated in FIG. 19, or a plurality of radial planes G21 to G25 illustrated in FIG. 20 may be determined. In addition, the number of faces of the tomographic plane is not limited to five, and is optional.

In step S6, it is determined whether the posterior capsule rupture is detected on the basis of the acquired tomographic image. More specifically, detection of posterior capsule rupture is performed, for example, by detecting a discontinuous portion in the posterior capsule of the tomographic image.

If it is determined in step S6 that the posterior capsule rupture is detected, the reporting information generation unit 212, in step S7, generates reporting information and supplies the reporting information to the reporting information presentation unit 202 under control of the control unit 211.

In step S8, the loudspeaker 67 serving as the reporting information presentation unit 202 outputs buzzer sound. The monitor 34 serving as the reporting information presentation unit 202 displays the tomographic image supplied from the reporting information generation unit 212. The tomographic image may be displayed after the surgeon's operation to display the tomographic image as described above.

Here, the tomographic image displayed as the reporting information is a tomographic image after the posterior capsule rupture, not a tomographic image at a moment when the posterior capsule is ruptured. Thus, the reporting information generation unit 212 holds (records) a tomographic image at a predetermined time in the past. When reproduction of the image is requested from the surgeon, the reporting information presentation unit 202 may be caused to present a moving image of a tomographic image in a predetermined period including a moment when the posterior capsule rupture is detected or a tomographic image (still image) at a moment when the posterior capsule rupture is detected.

Figure 21:
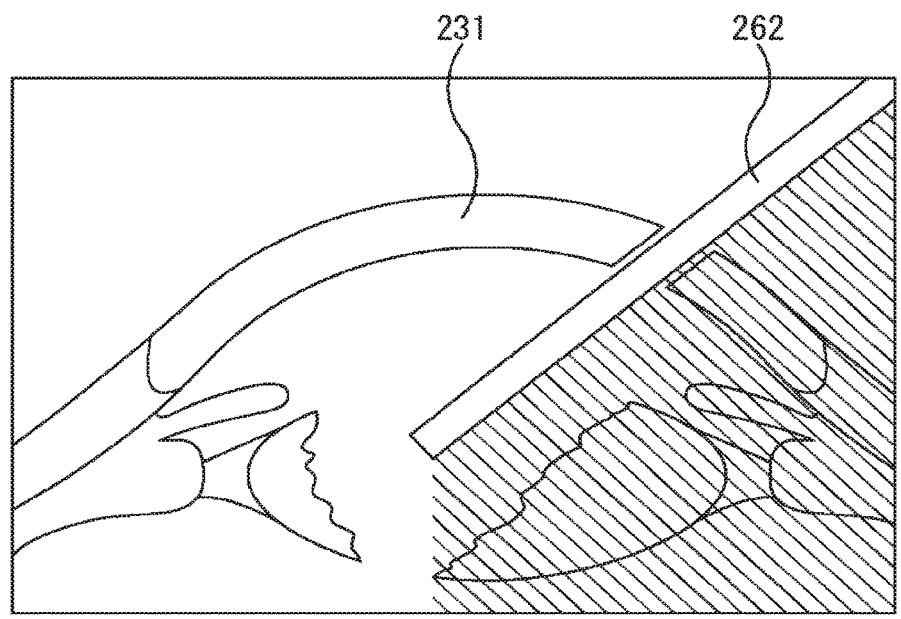
FIG. 21 is a diagram illustrating an example of a tomographic image in detecting posterior capsule rupture.

FIG. 21 illustrates an example of a tomographic image after the posterior capsule rupture, which is displayed on the monitor 34 as the reporting information. In the tomographic image, the lower side of the surgical tool 262 is shadowed because the tomographic information fails to be acquired from that region.

Furthermore, in detecting the posterior capsule rupture, in step S7, the control unit 211 can perform control to stop the operation of the ultrasonic phacoemulsification instrument 261 illustrated in FIG. 10 by outputting the device control information to the external device. More specifically, the device control information generation unit 215 can perform control to stop the ultrasound and aspiration at the time of the ultrasonic phacoemulsification and to stop the aspiration at the time of irrigation or aspiration (I/A).

The dangerous condition detection and reporting processing for detecting the posterior capsule rupture and reporting it to the surgeon as described above makes it possible to detect complications at an early stage and to manage it quickly, thereby preventing falling into a critical condition. In addition, when the posterior capsule rupture is detected, the device control information used to control the external device can be output to the external device, and thus it can contribute to preventing falling into a critical condition at the time of occurrence of complications.

<7. Detection Example of Nucleus Drop>

Next, detection of nucleus drop of the item (4) is described.

In the case where the nucleus drop is detected as the dangerous condition detection and reporting processing, the dangerous condition detection and reporting processing on the nucleus drop starts from the time when the posterior capsule rupture is detected.

Figure 22:
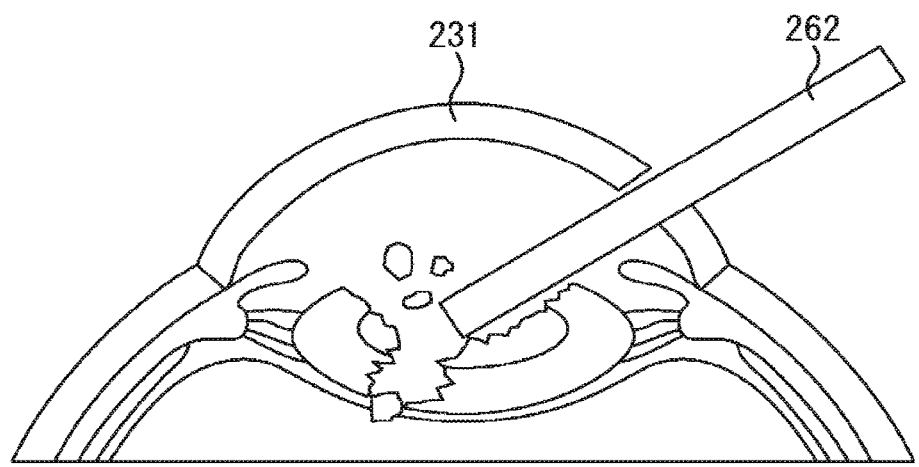
FIG. 22 is a diagram illustrated to describe nucleus drop.

As illustrated in FIG. 22, the nucleus drop occurs from a point in which the posterior capsule is ruptured, and so the control unit 211 sets a tomographic capturing space around a position of the posterior capsule rupture and determines the tomographic plane in step S3. Specifically, similarly to the case where the posterior capsule rupture is detected, the plurality of planes G21 to G25 parallel to the longitudinal direction of the surgical tool 262 illustrated in FIG. 16, the plurality of planes G21 to G25 perpendicular to the longitudinal direction of the surgical tool 262 illustrated in FIG. 18, the plurality of planes G21 to G25 having a predetermined angle in the longitudinal direction of the surgical tool 262 illustrated in FIG. 19, the plurality of radial planes G21 to G25 illustrated in FIG. 20, or the like, can be determined as the tomographic plane around the position of the posterior capsule rupture. Even when the eye moves, the tomographic plane is determined to follow the position of the posterior capsule rupture using the image recognition.

In step S6, it is determined whether the nucleus drop is detected on the basis of the acquired tomographic image. The control unit 211 detects that a nucleus drop occurs at the position of the posterior capsule rupture in the tomographic image in the case where an object having a large scattering passes from the top to the bottom. Moreover, in the case where the size of a dropped object (nucleus) is equal to or smaller than a predetermined size, the dropped object does not affect the prognosis, so the nucleus drop is not necessarily detected.

If it is determined in step S6 that the nucleus drop is detected, the reporting information generation unit 212, in step S7, generates reporting information and supplies the reporting information to the reporting information presentation unit 202 under control of the control unit 211.

In step S8, the loudspeaker 67 serving as the reporting information presentation unit 202 outputs buzzer sound. The monitor 34 serving as the reporting information presentation unit 202 displays the tomographic image supplied from the reporting information generation unit 212. Moreover, the tomographic image may be displayed after the surgeon's operation to display the tomographic image as described above.

The tomographic image at the time of presentation of the reporting information is the tomographic image obtained after the nucleus drop, and so it is not a tomographic image at a moment when the nucleus is dropped. Thus, the reporting information generation unit 212 holds (records) a tomographic image at a predetermined time in the past. When reproduction of the image is requested from the surgeon, the reporting information presentation unit 202 may be caused to present a moving image of a tomographic image in a predetermined period including a moment when the nucleus drop is detected or a tomographic image (still image) at a moment when the nucleus drop is detected.

Figure 23:
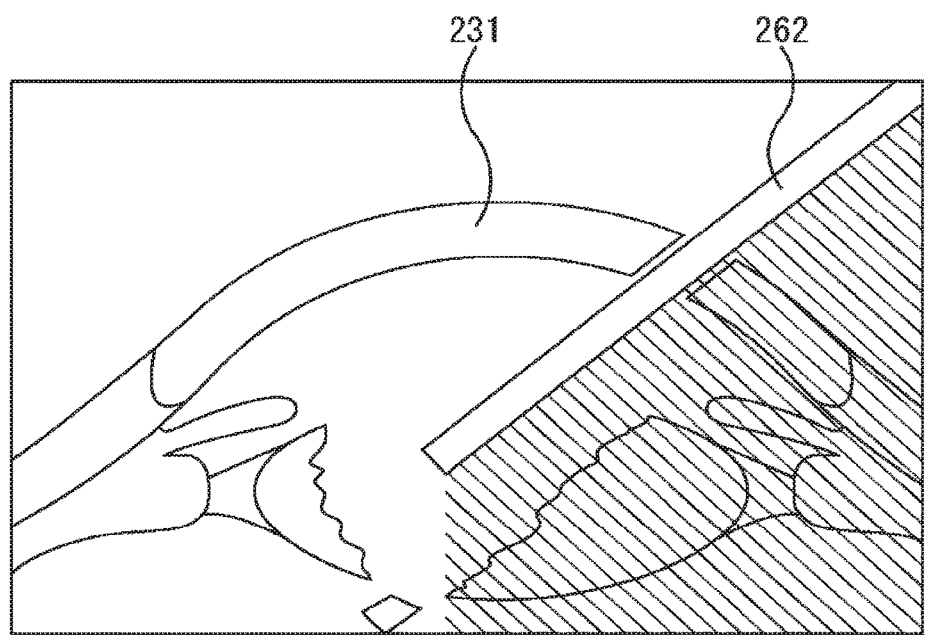
FIG. 23 is a diagram illustrating an example of a tomographic image in detecting nucleus drop.

FIG. 23 illustrates an example of the tomographic image at the time of the nucleus drop displayed on the monitor 34 as the reporting information. In the tomographic image, the lower side of the surgical tool 262 is shadowed because the tomographic information fails to be acquired from that region.

The dangerous condition detection and reporting processing for detecting the nucleus drop and reporting it to the surgeon as described above makes it possible to perform an appropriate treatment against the nucleus drop, specifically, in one example, to prompt the surgeon to carry out the vitreous surgery, thereby reducing the possibility that a treatment for complications are omitted.

<8. Detection Example of Implant Misplacement>

Next, detection of implant misplacement of the item (5) is described. In the following description is given of a case where the implant is an intraocular lens as an example.

Figure 24:
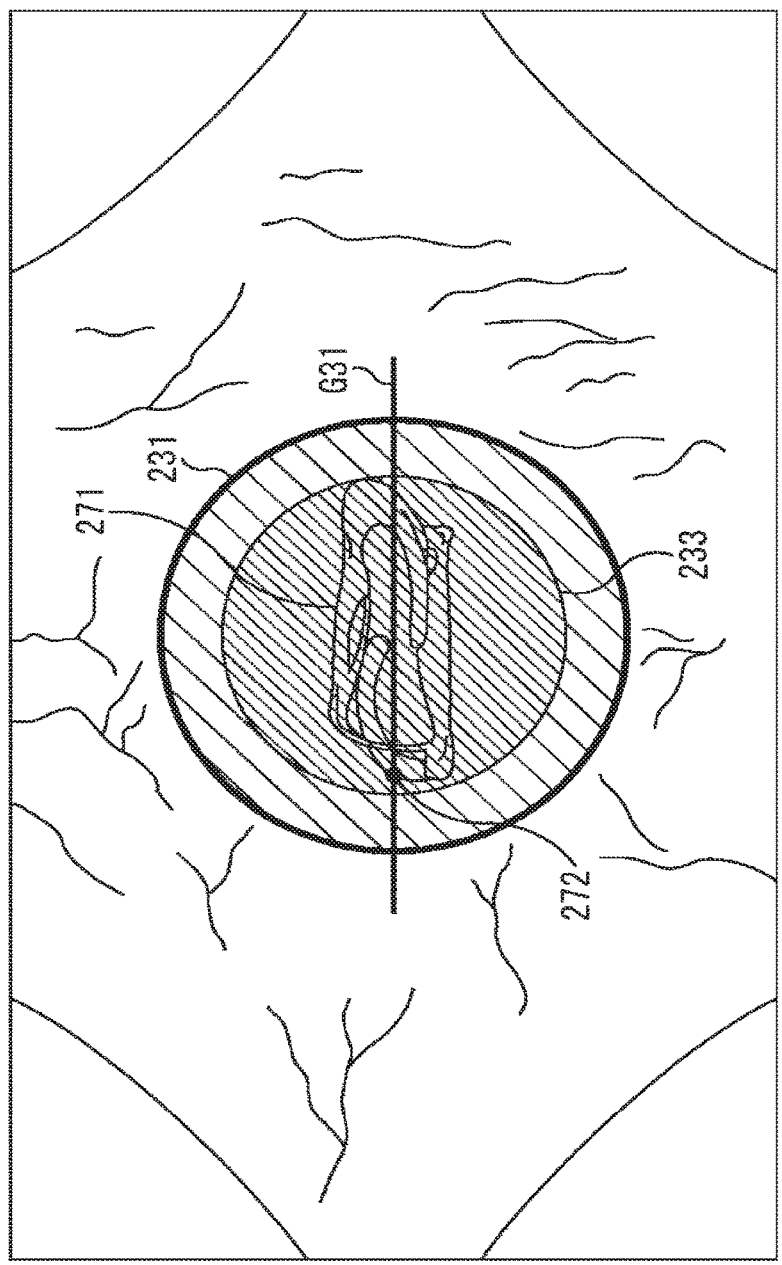
FIG. 24 is a diagram illustrated to describe determination of a tomographic plane in detecting implant misplacement.

In detecting the implant misplacement, the control unit 211 determines a plane G31 as the tomographic plane in step S3 of the dangerous condition detection and reporting processing. The plane G31 passes through a specific portion 272 (an end portion in the longitudinal direction) of an intraocular lens 271 recognized from the front image and is parallel to the longitudinal direction, as illustrated in FIG. 24. Then, the control unit 211 generates tomographic plane specifying information used to specify the determined tomographic plane and supplies the information to the image information acquisition unit 201.

In step S4, the image information acquisition unit 201 acquires a tomographic image on the basis of the tomographic plane specifying information supplied from the control unit 211, and supplies the tomographic image to the control unit 211.

Figure 25:
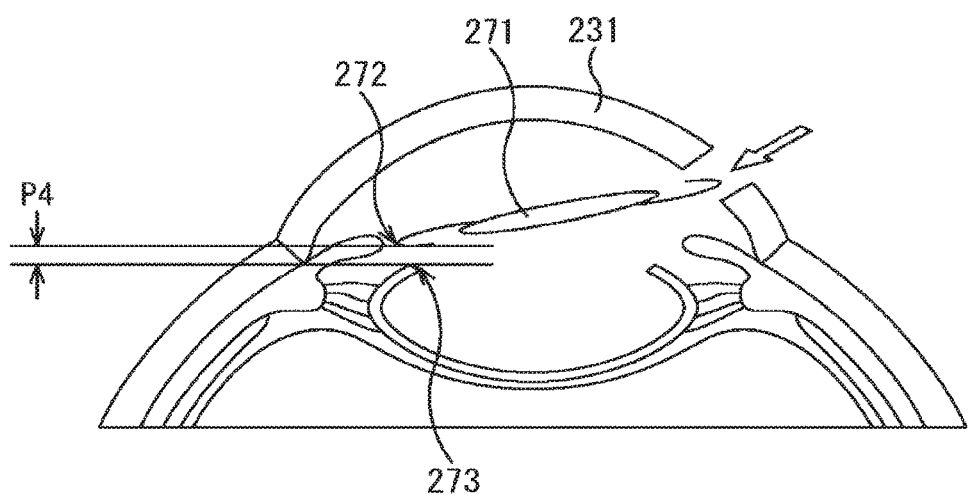
FIG. 25 is a diagram illustrated to describe a risk parameter in detecting implant misplacement.

In step S5, the control unit 211 calculates, as the risk parameter, a distance P4 from the specific portion 272 of the intraocular lens 271 to an upper end 273 of the lens capsule (e.g., the distance in perpendicular direction), as illustrated in FIG. 25, on the basis of the tomographic image supplied from the image information acquisition unit 201.

Figure 26:
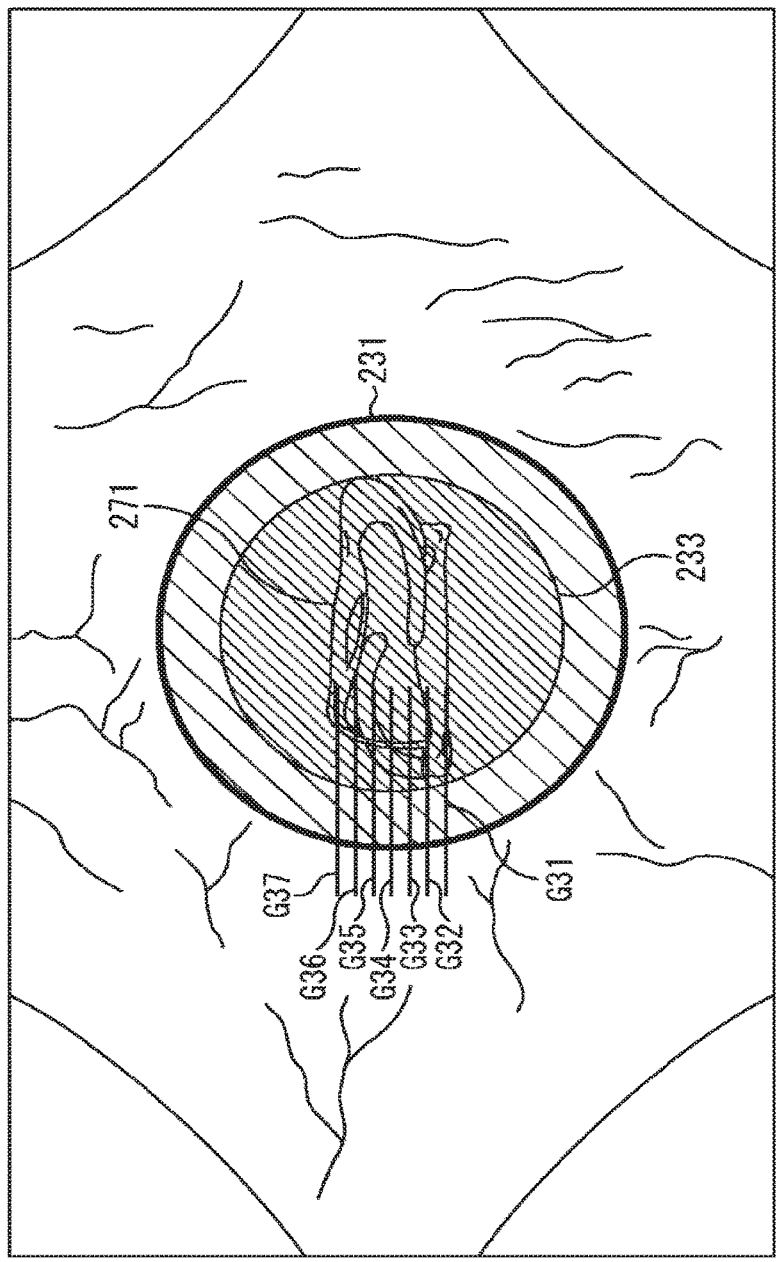
FIG. 26 is a diagram illustrated to describe determination of a tomographic plane in detecting implant misplacement.

The processing procedures from steps S1 to S9 (case of being determined as NO in step S6) are repeated until the risk parameter reaches a value smaller than a predetermined value. Then, when the distance P4 from the specific portion 272 of the intraocular lens 271 to the upper end 273 of the lens capsule comes close to predetermined proximity, the control unit 211 determines the tomographic plane in step S3, so that the capturing range of the tomographic plane is narrow and its density is high, as illustrated in FIG. 26. In the example of FIG. 26, a plurality of planes G31 to G37 are determined so that the tomographic planes are formed in the longitudinal direction near the specific portion 272 of the intraocular lens 271. The number and density of the tomographic planes, the size of the tomographic capturing space, the direction of the tomographic plane, and the like are not limited to this example and can be optionally determined. In addition, the tomographic plane may be changed appropriately depending on the calculated risk parameter (the distance P4 from the specific portion 272 of the intraocular lens 271 to the upper end 273 of the lens capsule).

Figure 27:
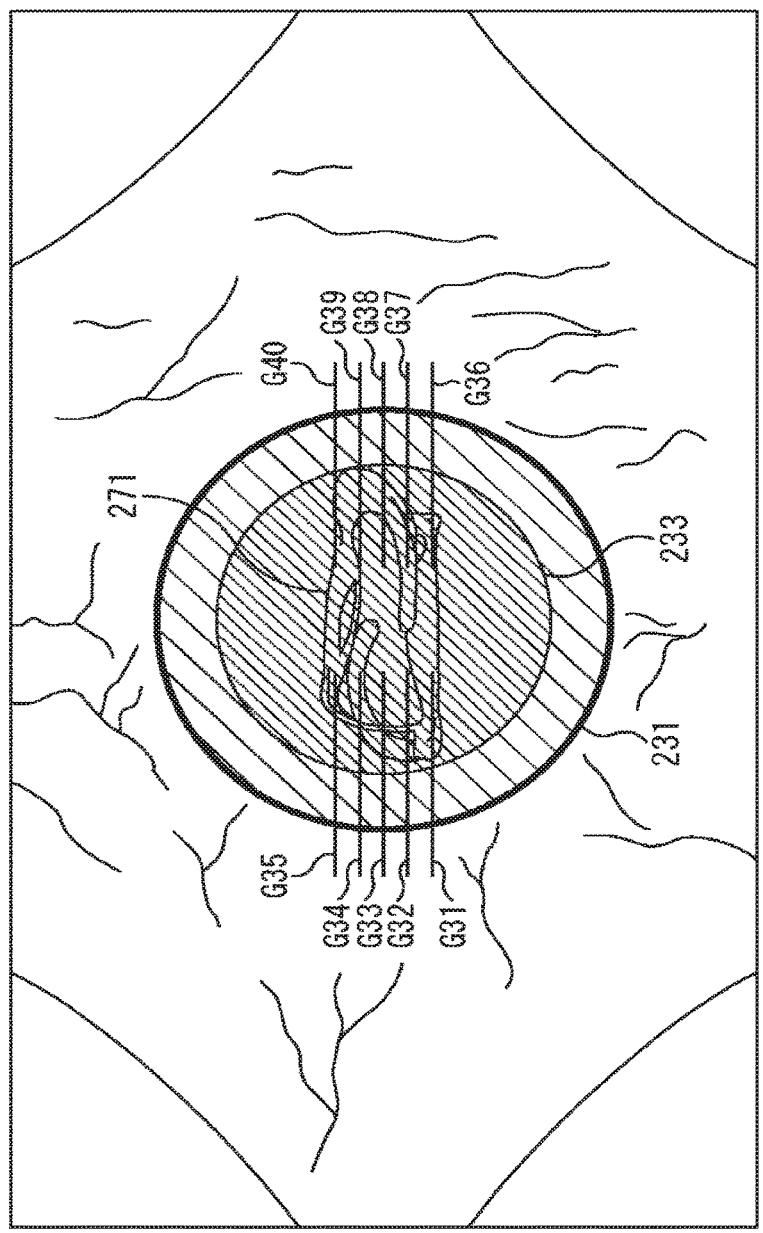
FIG. 27 is a diagram illustrated to describe determination of a tomographic plane in detecting implant misplacement.

Further, there may be a case where there are two points in which the distance P4 from the specific portion 272 of the intraocular lens 271 to the upper end 273 of the lens capsule is close to a predetermined value or less. In this case, the control unit 211 determines a plurality of planes G31 to G40 so that the tomographic planes are formed at each of the points where the risk parameter is equal to or less than a predetermined value, as illustrated in FIG. 27. In the example of FIG. 27, the plurality of planes G31 to G35 are set for the first point, and the plurality of planes G36 to G40 are set for the second point.

In this way, even in detecting the implant misplacement, the tomographic plane is also dynamically determined (changed) depending on the risk parameter that varies during surgery.

In step S6, it is determined whether the implant misplacement is detected on the basis of the acquired tomographic image. In other words, it is determined, on the basis of the tomographic image, whether the intraocular lens 271 (or a capsular tension ring (CTR)) to be placed in the lens capsule is set on the lens capsule.

In the case where it is determined in step S6 that the implant misplacement is detected, the reporting information generation unit 212, in step S7, generates reporting information and supplies the reporting information to the reporting information presentation unit 202 under control of the control unit 211.

In step S8, the loudspeaker 67 serving as the reporting information presentation unit 202 outputs buzzer sound under the control of the control unit 211. The monitor 34 serving as the reporting information presentation unit 202 displays the tomographic image supplied from the reporting information generation unit 212. Moreover, the tomographic image may be displayed after the surgeon's operation to display the tomographic image as described above.

Figure 28:
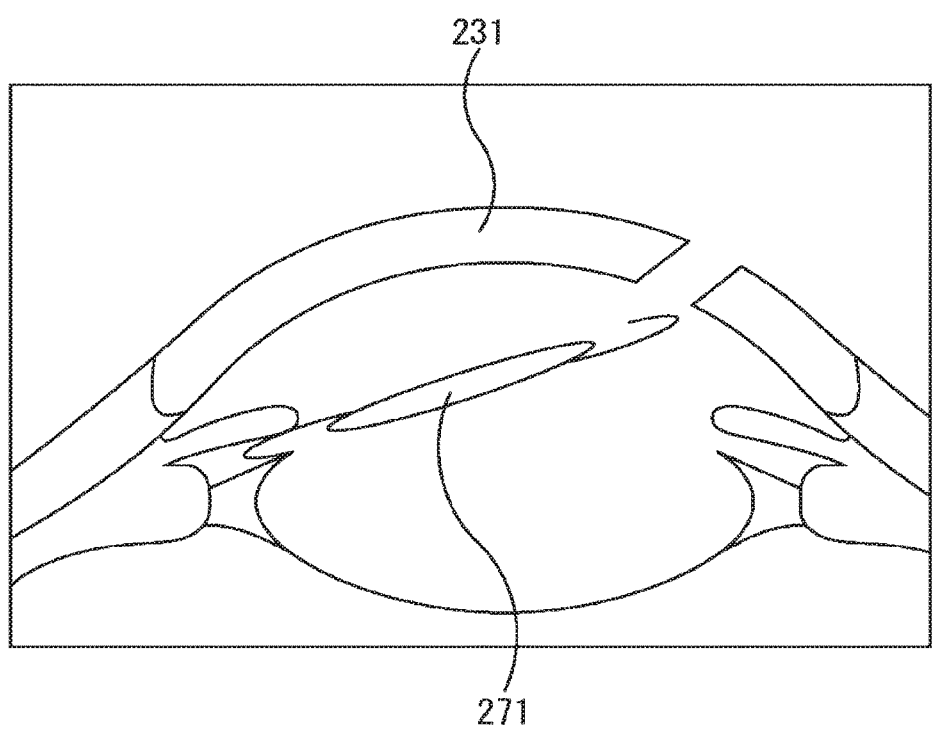
FIG. 28 is a diagram illustrating an example of a tomographic image in detecting implant misplacement.

FIG. 28 illustrates an example of a tomographic image after detection of the implant misplacement, which is displayed on the monitor 34 as the reporting information.

The dangerous condition detection and reporting processing for detecting the implant misplacement and reporting it to the surgeon as described above makes it possible to detect erroneous treatment at an early stage and to carry out desirable treatment.

<9. Detection Example of Iris Prolapse Risk>

Next, detection of an iris prolapse risk of the item (6) is described.

Figure 29:
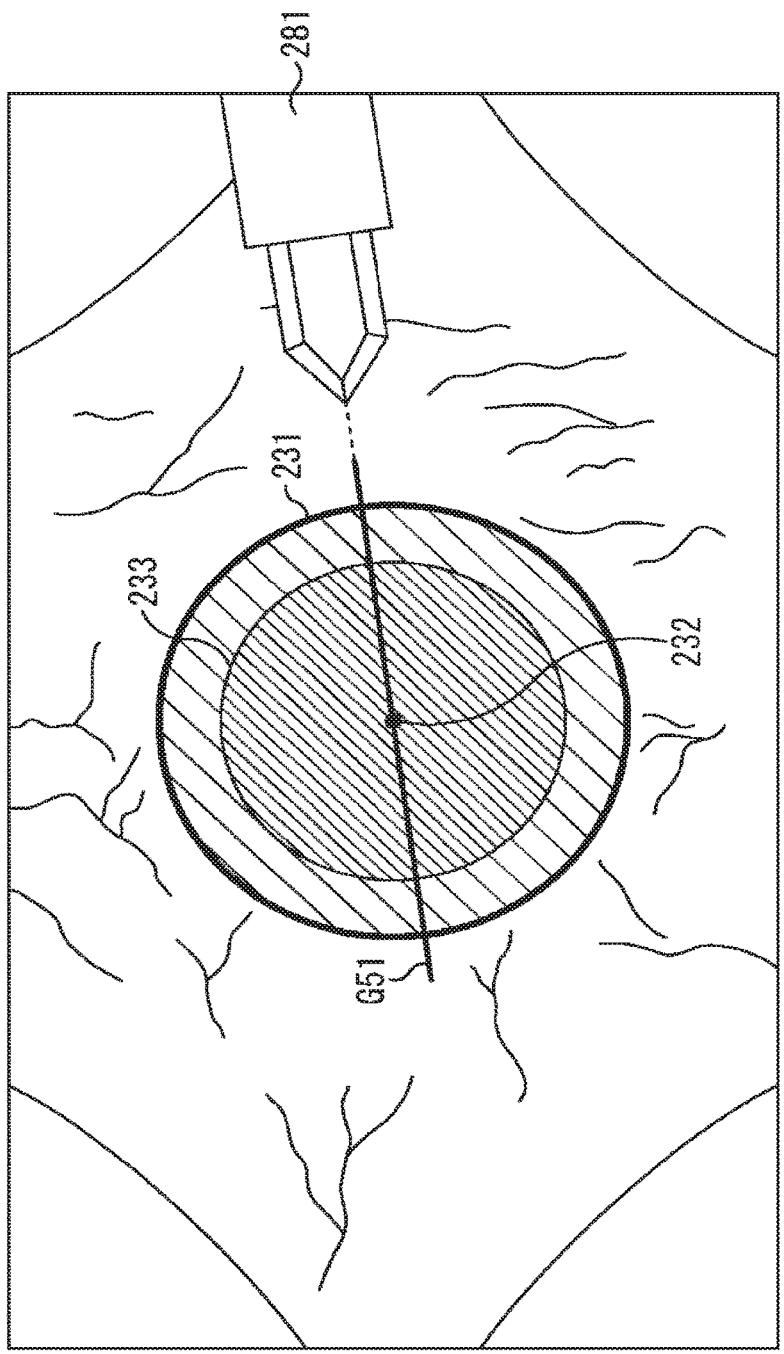
FIG. 29 is a diagram illustrated to describe determination of a tomographic plane in detecting an iris prolapse risk.

In detecting the iris prolapse risk, in the processing of step S3 until forming of the incision is complete among the steps S1 to S9 of the repeatedly executed dangerous situation detection and reporting processing, the control unit 211 determines the center position 232 of the cornea 231 recognized from the front image and a plane G51 passing through the tip of a surgical tool 281 as the tomographic plane, as illustrated in FIG. 29. Then, the control unit 211 generates tomographic plane specifying information used to specify the determined tomographic plane and supplies it to the image information acquisition unit 201.

Moreover, in the case where the control unit 211 detects that the surgical tool 281 enters the cornea 231 and then exits the cornea 231, the control unit 211 can determined that the forming of the incision is completed.

Figure 30:
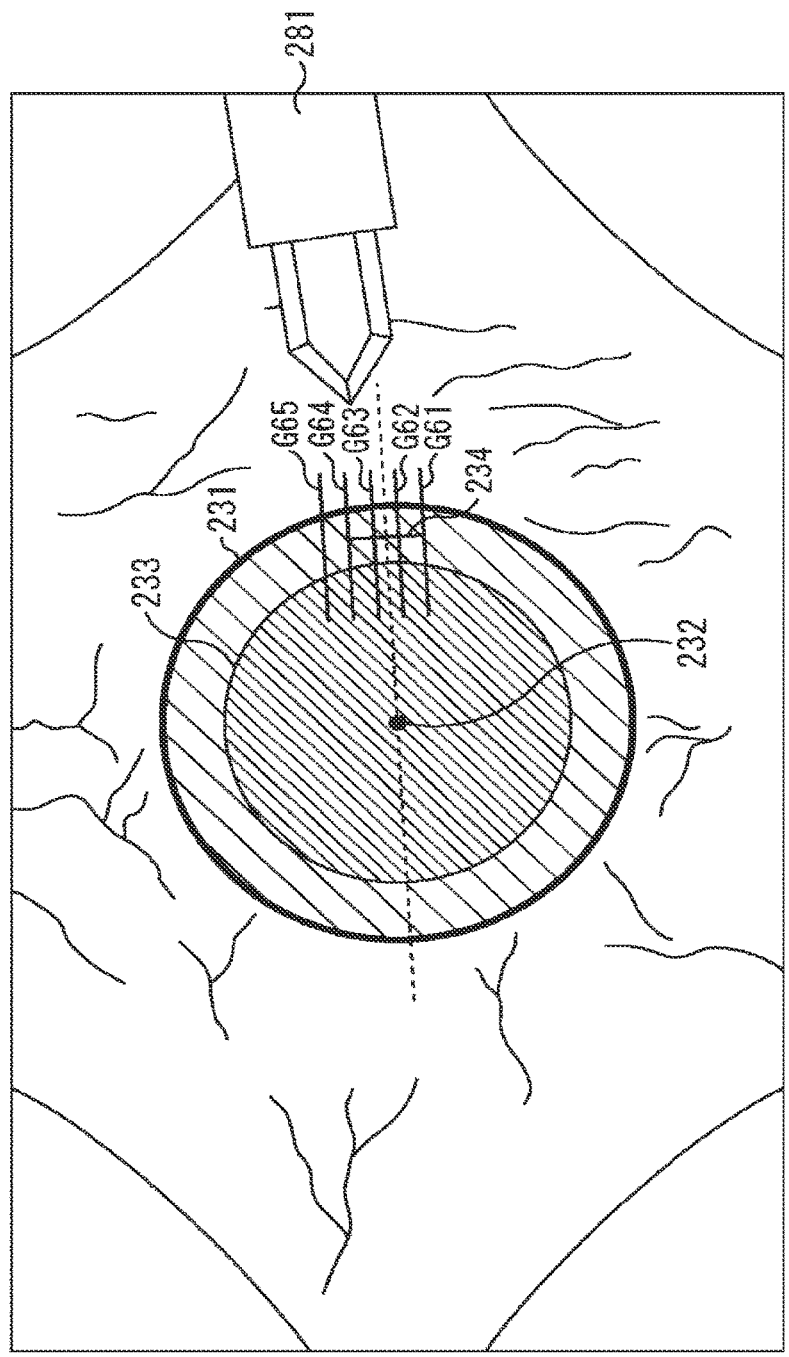
FIG. 30 is a diagram illustrated to describe determination of a tomographic plane in detecting an iris prolapse risk.

Then, in the processing of step S3 after completion of the forming of the incision, the control unit 211 determines a tomographic plane having the tomographic capturing space around the position 234 of the incision as illustrated in FTG. 30. In FIG. 30, a plurality of planes G61 to G65, which are parallel to a line (line indicated by a broken line in the figure) passing through the center position 232 of the cornea 231, are determined as the tomographic plane. Then, the control unit 211 generates tomographic plane specifying information used to specify the determined tomographic plane and supplies it to the image information acquisition unit 201.

In step S4, the image information acquisition unit 201 acquires a tomographic image on the basis of the tomographic plane specifying information supplied from the control unit 211, and supplies the tomographic image to the control unit 211. The control unit 211 performs control so that the tomographic images of the plurality of planes G61 to G65 are acquired over a fixed period of time or more. In the case where the acquisition rate of the tomographic image is controlled, for example, so that 30 tomographic images per second are acquired or the tomographic image is acquired during at least ⅓ second or more, ten sets of tomographic images of each of the planes G61 to G65 are obtained.

Figure 31:
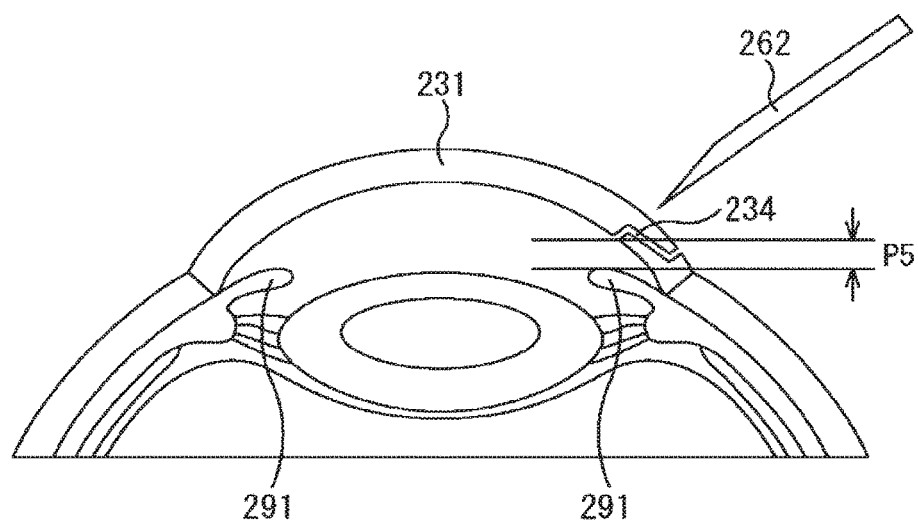
FIG. 31 is a diagram illustrated to describe a risk parameter in detecting an iris prolapse risk.

In step S5, the control unit 211 calculates, as the risk parameter, a distance P5 from the position 234 of the incision on the endothelial side of the cornea 231 to a iris 291 (e.g., the distance in perpendicular direction), as illustrated in FIG. 31, on the basis of the tomographic image supplied from the image information acquisition unit 201.

In step S6, the control unit 211 determines whether the distance P5 from the position 234 of the incision on the endothelial side of the cornea 231 to the iris 291 as the risk parameter is shorter than a preset threshold. Thus, the control unit 211 determines whether the dangerous condition, that is, the iris prolapse risk is detected.

If it is determined in step S6 that the distance P5 from the position 234 of the incision on the endothelial side of the cornea 231 to the iris 291 is shorter than the predetermined threshold and the iris prolapse risk is detected, the reporting information generation unit 212 generates reporting information and supplies it to the reporting information presentation unit 202 under the control of the control unit 211, in step S7.

In step S8, the loudspeaker 67 serving as the reporting information presentation unit 202 outputs buzzer sound. The monitor 34 serving as the reporting information presentation unit 202 displays the tomographic image supplied from the reporting information generation unit 212. Moreover, the tomographic image may be displayed after the surgeon's operation to display the tomographic image as described above.

Figure 32:
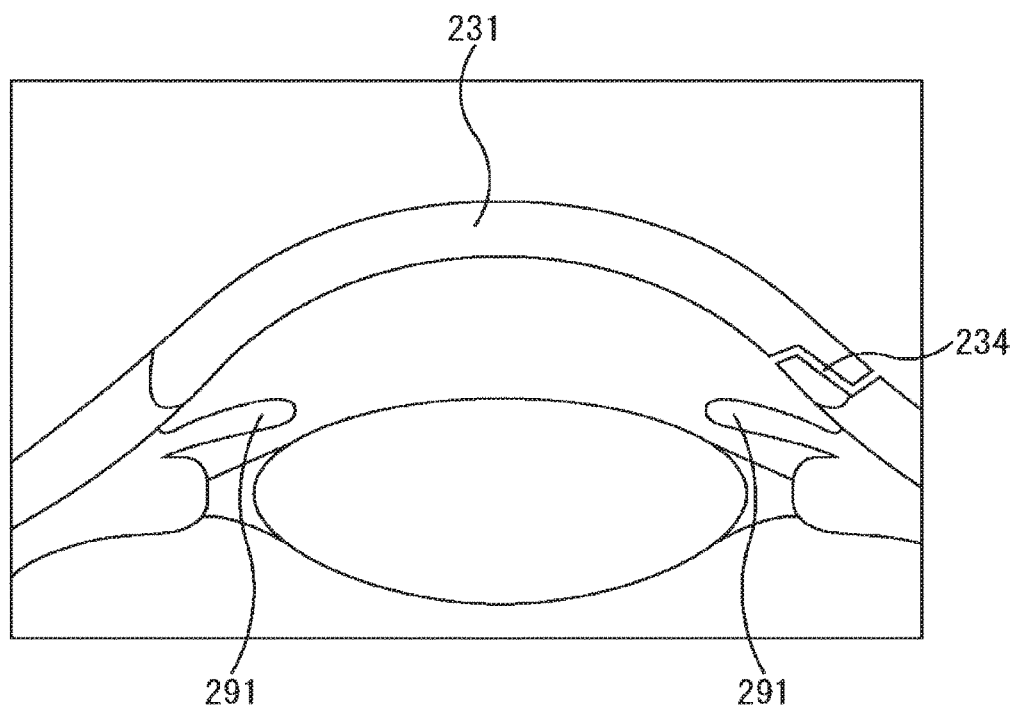
FIG. 32 is a diagram illustrating an example of a tomographic image in detecting an iris prolapse risk.

FIG. 32 illustrates an example of a tomographic image displayed on the monitor 34 as the reporting information.

The dangerous condition detection and reporting processing for detecting the iris prolapse risk and reporting it to the surgeon as described above makes it possible to detect a condition that is likely to cause the iris prolapse that is a complication, and to take appropriate measures to avoid the complication, as a specific example, to prompt the surgeon to re-form the incision. Thus, the occurrence of complications can be prevented.

As described above, according to the surgery system 11 of FIG. 1, it is possible to detect the above-described six types of dangerous conditions during the cataract surgery, that is, (1) shallow anterior chamber, (2) IMS risk, (3) posterior capsule rupture, (4) nucleus drop, (5) implant misplacement, and (6) iris prolapse risk, to report them to the surgeon, or to control the external device. This makes it possible to prevent the occurrence of complications and to prevent falling into a critical condition at the time of occurrence of complications.

Moreover, the six types of dangerous conditions are described individually in the above description, but the surgery system 11 can execute the dangerous condition detection and reporting processing for detecting two or more types of dangerous conditions at the same time (in parallel).

In the dangerous condition detection and reporting processing for detecting each dangerous condition as described above, a plurality of tomographic planes are determined at regular intervals in a predetermined tomographic capturing space to acquire a plurality of tomographic images. However, it may be possible to acquire volume data 292 illustrated in FIG. 33 by causing intervals in which the tomographic planes are acquired to be close.

Figure 33:
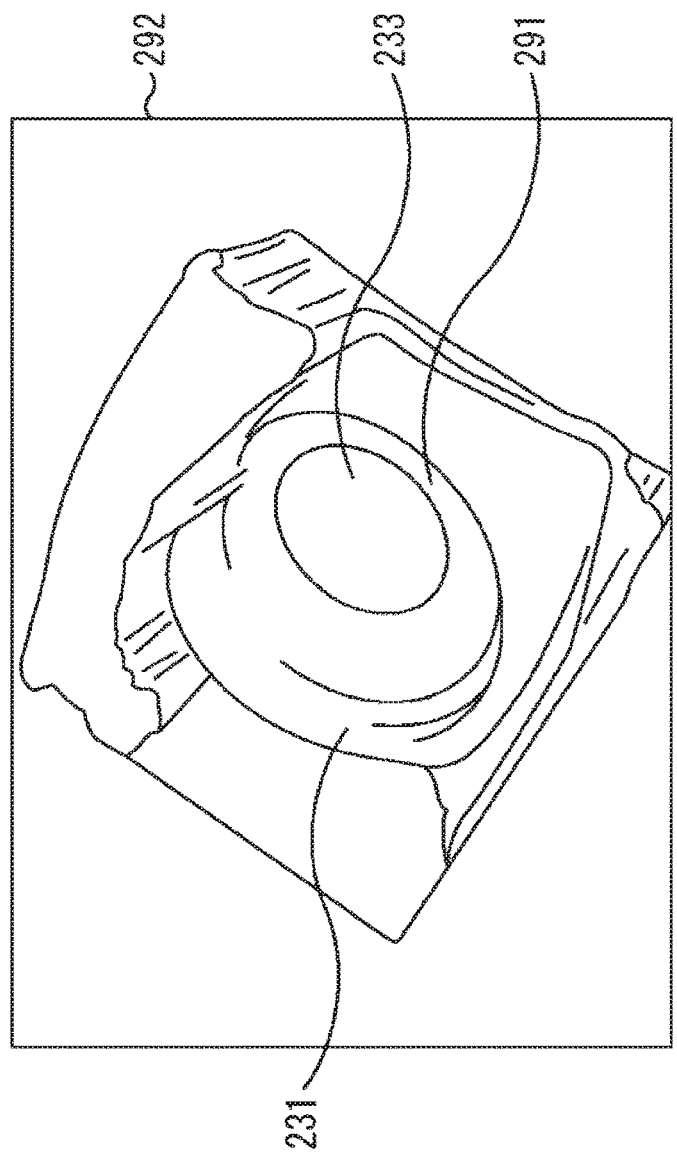
FIG. 33 is a diagram illustrating an example of volume data.

The volume data 292 of FIG. 33 is a stereoscopic image obtained by accumulating tomographic images at the positions of the tomographic planes by setting intervals between a plurality of tomographic planes parallel to each other to be close. In the case where the image processing device 33 has the volume data 292 of the eye during the surgery, the surgeon can check any tomographic image by designating a predetermined tomographic plane.

In the dangerous condition detection and reporting processing for detecting each of the dangerous conditions described above, the image processing device 33 acquires the volume data 292 of a predetermined tomographic capturing space instead of acquiring a plurality of tomographic images, and may display a predetermined tomographic image in the volume data as the reporting information.

<10. Configuration Example of Computer>

The series of processing procedures described above can be executed by hardware but can also be executed by software. When the series of processing procedures are executed by software, a program that constructs such software is installed into a computer. Here, the term "computer" used herein includes, for example, a computer incorporated into dedicated hardware and a general-purpose personal computer capable of executing various functions by installing various programs.

Figure 34:
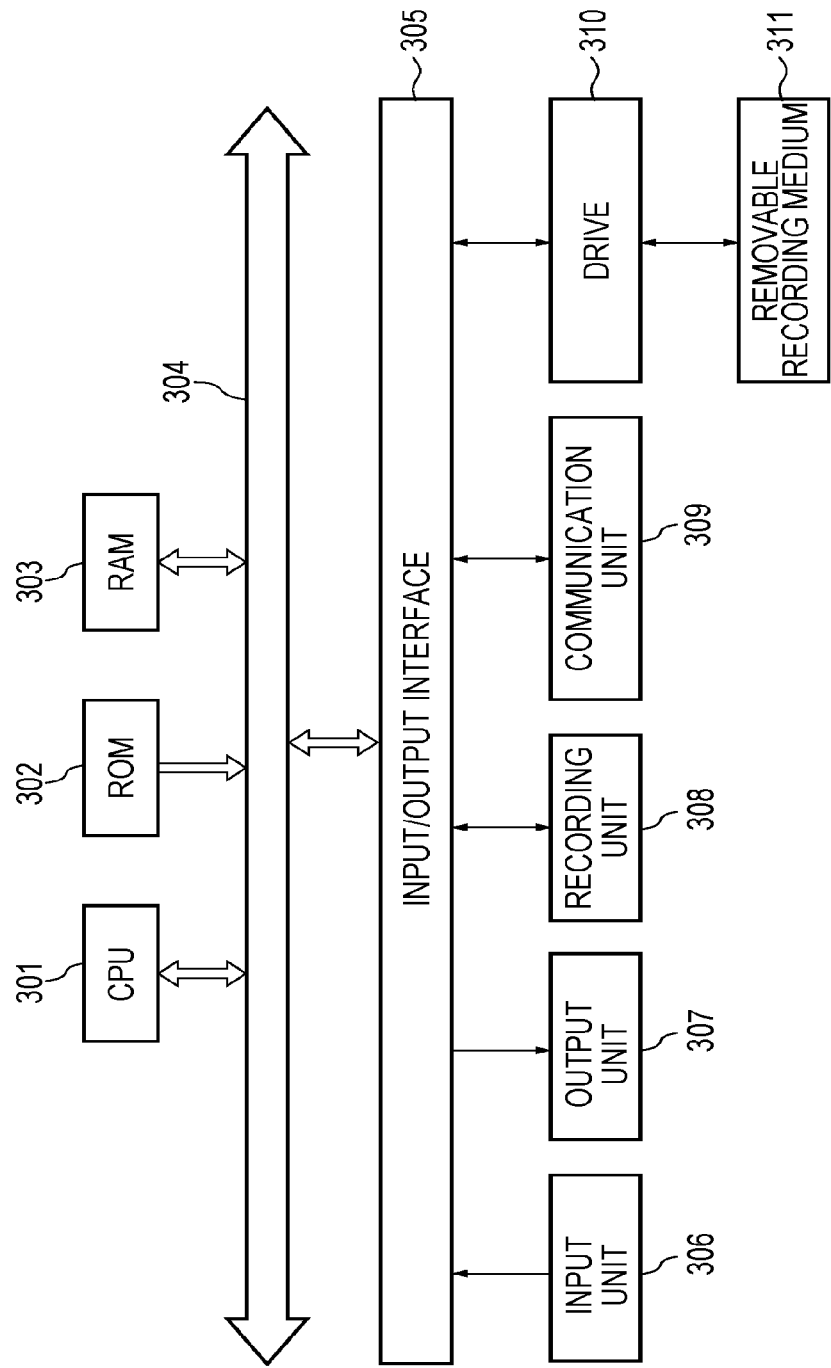
FIG. 34 is a block diagram illustrating a configuration example of an embodiment of a computer to which the present technology is applied.

FIG. 34 is a block diagram illustrating an example configuration of the hardware of a computer that executes the series of processing procedures described above in accordance with a program.

In the computer, a central processing unit (CPU) 301, a read only memory (ROM) 302, and a random access memory (RAM) 303 are interconnected via a bus 304.

The bus 304 is also connected to an input/output interface 305. The input/output interface 305 is connected to an input unit 306, an output unit 307, a recording unit 308, a communication unit 309, and a drive 310.

The input unit 306 is configured as a keyboard, a mouse, a microphone, an image sensor, or the like. The output unit 307 configured as a display, a loudspeaker, or the like. The recording unit 308 is configured as a hard disk, a non-volatile memory, or the like. The communication unit 309 is configured as a network interface or the like. The drive 310 drives a removable recording medium 311 such as a magnetic disk, an optical disk, a magneto-optical disk, a semiconductor memory, or the like.

In the computer configured as described above, in one example, the CPU 301 loads a program recorded in the recording unit 308 into the RAM 303 through the input/output interface 305 and the bus 304 and executes the program to carry out the series of processing procedures described earlier.

In one example, the program executed by the computer (the CPU 301) may be provided by being recorded on the removable recording medium 311 as a packaged medium or the like. The program can also be provided through a wired or wireless transmission medium, such as a local area network, the Internet, or a digital satellite broadcast.

In the computer, the program can be installed into the recording unit 308 through the input/output interface 305 by loading the removable recording medium 311 into the drive 310. It is also possible to receive the program from a wired or wireless transmission medium using the communication unit 309 and install the program into the recording unit 308. In another alternative, the program can be installed in advance into the ROM 302 or the recording unit 308.

Note that the program executed by the computer may be a program in which processing procedures are carried out in time series in the order described in this specification or may be a program in which processing procedures are carried out in parallel or at necessary timing, such as when the processing procedures are called.

The term "system" used herein has the meaning of a set of a plurality of components (e.g., a device or a module (part)), and does not take into account whether all components are in the same casing. Therefore, the system may be either a plurality of devices stored in separate casings and connected through a network or a plurality of modules within a single casing.

Further, the best modes of the present technology are not limited to the embodiments described above, and various changes and modifications may be made without departing from the scope of the present technology.

In one example, the present technology can employ a configuration of cloud computing in which one function is shared among a plurality of devices through a network and is processed in cooperation with each other.

Further, each processing step described in the above-mentioned flowcharts can be executed by one device, or can be executed by sharing it among a plurality of devices.

In addition, in the case where a plurality of processing procedures are included in one step, the plurality of processing procedures included in this one step can be executed by one device or by sharing it among a plurality of devices.

In addition, the effects described herein are not limiting but are merely examples, and there may be effects other than that described in the present specification.

Additionally, the present technology may also be configured as below.

(1)

An image processing device including:

a dangerous condition detection unit configured to detect a dangerous condition on the basis of a tomographic image of an eye acquired during surgery of the eye; and a control information generation unit configured to generate and output control information used to manage the detected dangerous condition.

(2)

The image processing device according to (1), in which the dangerous condition detection unit calculates a risk parameter on the basis of the tomographic image of the eye and detects the dangerous condition on the basis of the risk parameter.

(3)

The image processing device according to (1) or (2), in which the dangerous condition detection unit calculates a distance from a corneal vertex to an iridocorneal angle as the risk parameter and detects the dangerous condition.

(4)

The image processing device according to any of (1) to (3), in which the dangerous condition detection unit detects a shallow anterior chamber as the dangerous condition.

(5)

The image processing device according to any of (2) to (4), in which the dangerous condition detection unit calculates a distance from a corneal vertex to a lower end of a posterior capsule as the risk parameter and detects the dangerous condition.

(6)

The image processing device according to any of (1) to (5), in which the dangerous condition detection unit detects an IMS risk as the dangerous condition.

(7)

The image processing device according to any of (2) to (6), in which the dangerous condition detection unit calculates a distance from a specific portion of an implant to an upper end of a capsule as the risk parameter and detects the dangerous condition.

(8)

The image processing device according to any of (1) to (7), in which the dangerous condition detection unit detects implant misplacement as the dangerous condition.

(9)

The image processing device according to any of (2) to (8), in which the dangerous condition detection unit calculates a distance from a position of an incision of a cornea to an iris as the risk parameter and detects the dangerous condition.

(10)

The image processing device according to any of (1) to (9), in which the dangerous condition detection unit detects an iris prolapse risk as the dangerous condition.

(11)

The image processing device according to any of (1) to (10), in which the dangerous condition detection unit detects posterior capsule rupture as the dangerous condition.

(12)
The image processing device according to any of (1) to (11),
in which the dangerous condition detection unit detects nucleus drop as the dangerous condition.
(13)
The image processing device according to any of (1) to (12), further including:
a tomographic image determination unit configured to determine a capture plane of the tomographic image of the eye to be acquired on the basis of a front image of the eye.
(14)
The image processing device according to (13),
in which the tomographic image determination unit determines a plane passing through a center position of a range of a cornea as the capture plane.
(15)
The image processing device according to (13) or (14),
in which the tomographic image determination unit determines a plane passing through a tip of a surgical tool and being parallel to a longitudinal direction of the surgical tool as the capture plane.
(16)
The image processing device according to any of (13) to (15),
in which the tomographic image determination unit determines a plane passing through a specific portion of an implant as the capture plane.
(17)
The image processing device according to any of (13) to (16),
in which the tomographic image determination unit determines the capture plane of the tomographic image of the eye further on the basis of the tomographic image acquired previously.
(18)
The image processing device according to any of (13) to (17),
in which the tomographic image determination unit dynamically determines the capture plane of the tomographic image of the eye to be acquired during surgery of the eye.
(19)
The image processing device according to any of (1) to (18),
in which the control information generation unit generates and outputs reporting information used to report the dangerous condition to a surgeon as the control information used to manage the dangerous condition.
(20)
The image processing device according to (19),
in which the control information generation unit displays a moving image or a still image of the acquired tomographic image as the reporting information.
(21)
The image processing device according to any of (1) to (20),
in which the control information generation unit generates and outputs device control information used to control an external device as the control information used to manage the dangerous condition.
(22)
A method of image processing, the method including the steps of:
detecting, by an image processing device, a dangerous condition on the basis of a tomographic image of an eye acquired during surgery of the eye; and generating and outputting, by the image processing device, control information used to manage the detected dangerous condition.
(23)
A surgical microscope including:
a tomographic image capturing unit configured to capture a tomographic image of an eye as a target of surgery;
a dangerous condition detection unit configured to detect a dangerous condition on the basis of the tomographic image of the eye acquired during surgery; and
a control information generation unit configured to generate and output control information used to manage the detected dangerous condition.

REFERENCE SIGNS LIST 11 surgical system
21 surgical microscope
33 image processing device
34 monitor
63 front image capturing unit
64 tomographic image capturing unit
65 presentation unit
66 interface unit
67 loudspeaker
201 image information acquisition unit
202 reporting information generation unit
211 control unit
212 reporting information generation unit,
213 tomographic image determination unit
214 dangerous condition detection unit
215 device control information generation unit
231 cornea
232 center position
233 pupil
241 corneal vertex
242 iridocorneal angle
243 surgical tool
244 lower end of posterior capsule
261 ultrasonic phacoemulsification instrument
262 surgical tool
271 intraocular lens
272 specific portion
273 upper end of lens capsule
291 iris
301 CPU
302 ROM
303 RAM
306 input unit
307 output unit
308 recording unit
309 communication unit
310 drive

The invention claimed is:
1. An image processing device comprising:
processing circuitry configured to
obtain, along one or more tomographic planes, a tomographic image of an eye, the tomographic image being acquired during surgery of the eye,
calculate a risk parameter based on positions of anatomical structures of the eye that are derived from the tomographic image and from a position of a surgical instrument to detect a dangerous condition on the basis of the tomographic image of an eye acquired during surgery of the eye; and
generate and output control information that, upon the risk parameter passing a predetermined threshold, signals a warning to a user, displays the tomographic image of the detected dangerous condition, and/or initiates a change to an irrigation fluid pressure or the position of the surgical instrument that reduces a likelihood of complications resulting from the detected dangerous condition.

2. The image processing device according to claim 1, wherein the processing circuitry calculates the risk parameter on the basis of the tomographic image of the eye and detects the dangerous condition on the basis of the risk parameter.

3. The image processing device according to claim 2, wherein the processing circuitry calculates a distance from a corneal vertex to an iridocorneal angle as the risk parameter and detects the dangerous condition.

4. The image processing device according to claim 1, wherein the processing circuitry detects a shallow anterior chamber as the dangerous condition.

5. The image processing device according to claim 2, wherein the processing circuitry calculates a distance from a corneal vertex to a lower end of a posterior capsule as the risk parameter and detects the dangerous condition.

6. The image processing device according to claim 1, wherein the processing circuitry detects an infusion misdirection syndrome (IMS) risk as the dangerous condition.

7. The image processing device according to claim 2, wherein the dangerous condition detection unit calculates a distance from a specific portion of an implant to an upper end of a capsule as the risk parameter and detects the dangerous condition.

8. The image processing device according to claim 1, wherein the processing circuitry detects implant misplacement as the dangerous condition.

9. The image processing device according to claim 2, wherein the processing circuitry calculates a distance from a position of an incision of a cornea to an iris as the risk parameter and detects the dangerous condition.

10. The image processing device according to claim 1, wherein the processing circuitry detects an iris prolapse risk as the dangerous condition.

11. The image processing device according to claim 1, wherein the processing circuitry detects posterior capsule rupture as the dangerous condition.

12. The image processing device according to claim 1, wherein the dangerous condition detection unit detects nucleus drop as the dangerous condition.

13. The image processing device according to claim 1, wherein the processing circuitry is further to determine a capture plane of the tomographic image of the eye to be acquired on the basis of a front image of the eye.

14. The image processing device according to claim 13, wherein the processing circuitry determines a plane passing through a center position of a range of a cornea as the capture plane.

15. The image processing device according to claim 13, wherein the processing circuitry determines a plane passing through a tip of a surgical tool and being parallel to a longitudinal direction of the surgical tool as the capture plane.

16. The image processing device according to claim 13, wherein the processing circuitry determines a plane passing through a specific portion of an implant as the capture plane.

17. The image processing device according to claim 13, wherein the processing circuitry determines the capture plane of the tomographic image of the eye further on the basis of the tomographic image acquired previously.

18. The image processing device according to claim 13, wherein the processing circuitry dynamically determines the capture plane of the tomographic image of the eye to be acquired during surgery of the eye.

19. The image processing device according to claim 1, wherein the processing circuitry generates and outputs reporting information used to report the dangerous condition to a surgeon as the control information used to reduce the likelihood of complications resulting from the dangerous condition.

20. The image processing device according to claim 19, wherein the processing circuitry displays a moving image or a still image of the acquired tomographic image as the reporting information.

21. The image processing device according to claim 1, wherein the processing circuitry generates and outputs device control information used to control an external device as the control information used to reduce the likelihood of complications resulting from the dangerous condition.

22. A method of image processing, the method comprising the steps of:
    Obtaining, along one or more tomographic planes, a tomographic image of an eye, the tomographic image being acquired during surgery of the eye,
    calculating a risk parameter based on positions of anatomical structures of the eye that are derived from the tomographic image and from a position of a surgical instrument, and detecting, by image processing circuitry, a dangerous condition on the basis of the tomographic image of an eye acquired during surgery of the eye; and
    generating and outputting, by the image processing circuitry, control information that, upon the risk parameter passing a predetermined threshold, signals a warning to a user, displays the tomographic image of the detected dangerous condition, and/or initiates a change to an irrigation fluid pressure or the position of the surgical instrument that reduces a likelihood of complications resulting from the detected dangerous condition.

23. A surgical microscope comprising:
    a tomographic imager configured to capture, along one or more tomographic planes, a tomographic image of an eye, during surgery of the eye; and
    processing circuitry configured to
        calculate a risk parameter based on positions of anatomical structures of the eye that are derived from the tomographic image and from a position of a surgical instrument detect a dangerous condition on the basis of the tomographic image of the eye acquired during surgery, and
        generate and output control information that, upon the risk parameter passing a predetermined threshold, signals a warning to a user, displays the tomographic image of the detected dangerous condition, and/or initiates a change to an irrigation fluid pressure or the position of the surgical instrument that reduces a likelihood of complications resulting from the detected dangerous condition.

* * * * *